US007256042B2

(12) United States Patent
Rambhatla et al.

(10) Patent No.: US 7,256,042 B2
(45) Date of Patent: Aug. 14, 2007

(54) PROCESS FOR MAKING HEPATOCYTES FROM PLURIPOTENT STEM CELLS

(75) Inventors: Lakshmi Rambhatla, Redwood City, CA (US); Melissa K. Carpenter, Castro Valley, CA (US)

(73) Assignee: Geron Corporation, Menlo Park, CA (US)

(*) Notice: Subject to any disclaimer, the term of this patent is extended or adjusted under 35 U.S.C. 154(b) by 122 days.

(21) Appl. No.: 10/001,267

(22) Filed: Oct. 31, 2001

(65) Prior Publication Data

US 2002/0160511 A1 Oct. 31, 2002

Related U.S. Application Data

(63) Continuation-in-part of application No. 09/718,308, filed on Nov. 20, 2001, and a continuation-in-part of application No. 09/872,182, filed on May 31, 2001, now Pat. No. 6,506,571, and a continuation-in-part of application No. PCT/US01/13471, filed on Apr. 26, 2001.

(60) Provisional application No. 60/200,095, filed on Apr. 27, 2000.

(51) Int. Cl.
  *C12N 5/00* (2006.01)
  *C12N 5/08* (2006.01)
  *C12N 5/02* (2006.01)

(52) U.S. Cl. .................. 435/377; 435/366; 435/370

(58) Field of Classification Search ............... 435/370, 435/366, 377, 405, 325, 363, 374, 404, 395
See application file for complete search history.

(56) References Cited

U.S. PATENT DOCUMENTS

| 5,030,105 | A | 7/1991 | Kuri-Harcuch et al. |
| 5,532,156 | A | 7/1996 | Talbot et al. |
| 5,559,022 | A | 9/1996 | Naughton et al. |
| 5,576,207 | A | 11/1996 | Reid et al. |
| 5,763,255 | A | 6/1998 | Swiderek et al. |
| 5,869,243 | A | 2/1999 | Jauregui et al. |
| 6,017,760 | A | 1/2000 | Jauregui et al. |

FOREIGN PATENT DOCUMENTS

| EP | 0 827 742 A1 | 3/1998 |
| EP | 0 827 743 A1 | 3/1998 |
| EP | 0 953 633 A1 | 11/1999 |
| WO | WO95/12665 | 5/1995 |
| WO | WO97/47307 | 12/1997 |
| WO | WO99/23885 | 5/1999 |
| WO | WO99/37150 | 7/1999 |
| WO | WO 00/03001 | 1/2000 |
| WO | WO 00/18239 | 4/2000 |
| WO | WO 00/22098 | 4/2000 |
| WO | WO 00/43498 | 7/2000 |
| WO | WO 00/50048 | 8/2000 |
| WO | WO 01/39784 | 6/2001 |
| WO | WO 01/49113 | 7/2001 |
| WO | WO 01/62901 | 8/2001 |

OTHER PUBLICATIONS

Moreadith et al. J. Mol. Med. 75:208-216 (1997).*
Pera et al. Journal of Cell Science 113: 5-10 (2000).*
Lee et al. Genesis, 38:32-38 (2004).*
Adams, R.M., et al., "Effective cryopreservation and long-term storage of primary human hepatocytes with recovery of viability, differentiation, and replicative potential", *Cell Transplantation*, 4(6):579-586 (1995).
Agelli, M., et al., "Putative liver progenitor cells: conditions for long-term survival in culture", *Histochemical Jounral*, 29:205-217 (1997).
Alison, M., "Liver stem cells: a two compartment system", *Cell Biology*, 10:710-715 (1998).
Baribault, H., et al., "Dexamethasone and dimethylsulfoxide as distinct regulators of growth and differentiation of cultured suckling rat hepatocytes", *J Cell Physiol*, 129(1):77-84 (1986).
Block, G.D., et al., "Population expansion, clonal growth, and specific differentiation patterns in primary cultures of hepatocytes induced by HGF/SF, EGF and TGF∝ in a chemically defined (HGM) medium", *J Cell Bio.*, 132(6)1133-1149 (1996).
Blouin, MJ., et al., "Specialization switch in differentiating embryonic rat liver progenitor cells in response to sodium butyrate", *Exp Cell Res*, 217(1):22-30 (1995).
Brill, S., et al., "Expansion conditions for early hepatic progenitor cells from embryonal and neonatal rat livers", *Dig Diseases & Sci*, 44(2):364-371 (Feb. 1999).
Buommino, E., et al., "Sodium butyrate/retinoic acid costimulation induces apoptosis-independent growth arrest and cell differentiation in normal and ras-transformed seminal vesicle epithelial cells unresponsive to retinoic acid", *J Mol Endocrinol* 24(1):83-94 (Feb. 2000).
Chen, WY., et al., "Reactivation of silenced, virally transduced genes by inhibitors of histone deacetylase", *Proc. Natl. Acad. Sci. USA*, 94:5798-5803 (May 1997).
Coghlan, A., "Highly Cultured", *New Scientist*, Aug. 19, 2000.

(Continued)

*Primary Examiner*—Thaian N. Ton
(74) *Attorney, Agent, or Firm*—David J. Earp

(57) ABSTRACT

It has been discovered that when pluripotent stem cells are cultured in the presence of a hepatocyte differentiation agent, a population of cells is derived that has a remarkably high proportion of cells with phenotypic characteristics of liver cells. In one example, human embryonic stem cells are allowed to form embryoid bodies, and then combined with the differentiation agent n-butyrate, optionally supplemented with maturation factors. In another example, n-butyrate is added to human embryonic stem cells in feeder-free culture. Either way, a remarkably uniform cell population is obtained, which is predominated by cells with morphological features of hepatocytes, expressing surface markers characteristic of hepatocytes, and having enzymatic and biosynthetic activity important for liver function. Since stem cells readily proliferate in culture, this system provides an abundant source of cells of the hepatocyte lineage for a variety of applications, such as drug screening, and replenishing liver function in the context of clinical treatment.

10 Claims, 7 Drawing Sheets

OTHER PUBLICATIONS

Figure 1:
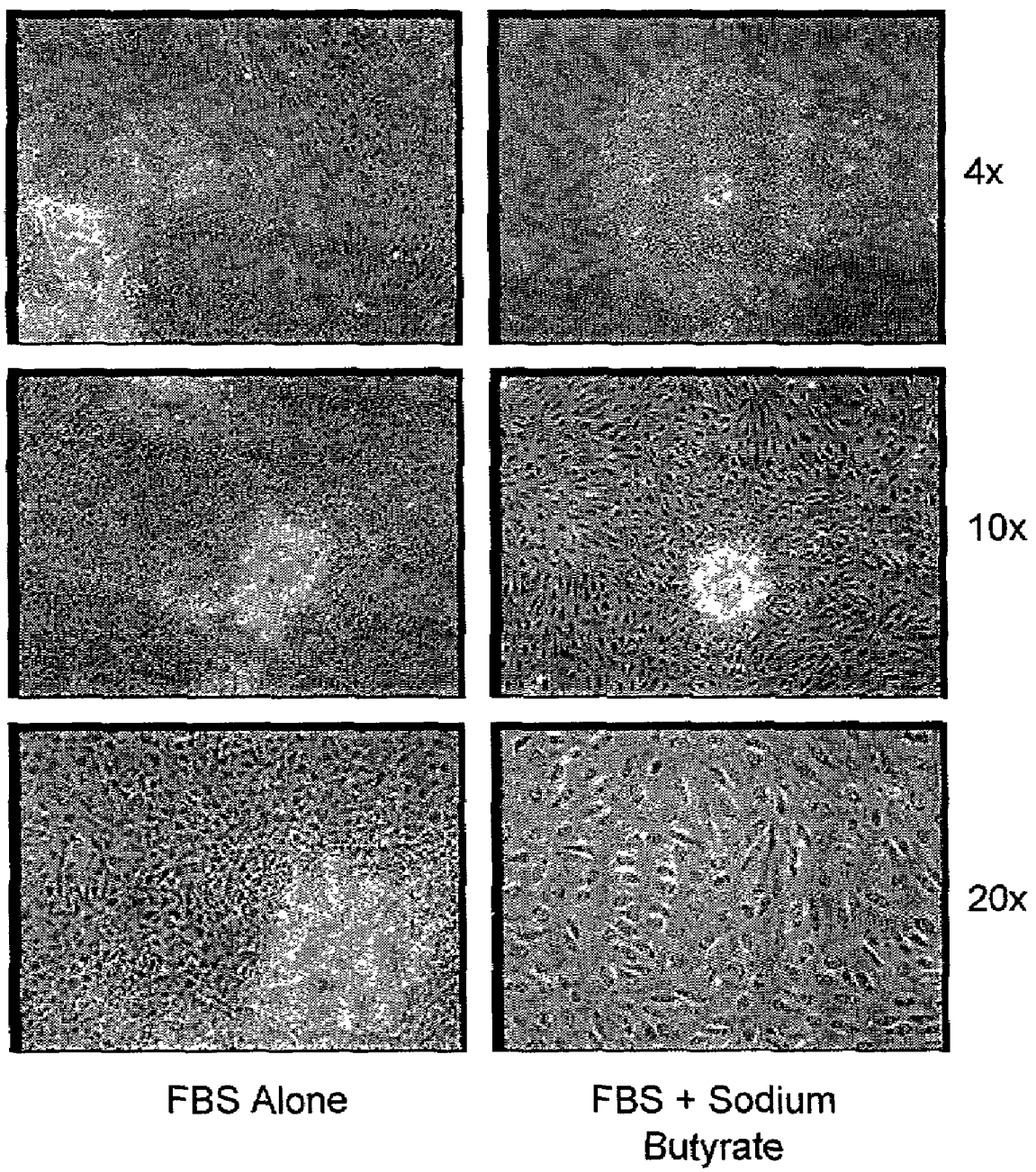

Coleman, W.B., et al., "Development of dexamethasone-inducible tyrosine aminotransferase activity in WB-F344 rat liver epithelial stemlike cells cultured in the presence of sodium butyrate", *J Cell Physiol*, 161(3):463-469 (Dec. 1994).

Davis, MG., et al., "Involvement of gialpha2 in sodium butyrate-induced erythroblastic differentiation of K562 cells", *Biochem J*, 1(346)Pt2:455-461 (Mar. 2000).

Devereux, T.R., et al., "DNA methylation analysis of the promoter region of the human telomerase reverse transcriptase (hTERT) gene", *Cancer Research*, 59:6087-6090,(Dec. 1999).

Enat, R., et al., "Hepatocyte proliferation in vitro: Its dependence on the use of serum-free hormonally defined medium and substrata of extracellular matrix", *Proc. Natl. Acad. Sci. USA*, 81:1411-1415 (Mar. 1984).

Engelmann, G.L., et al., "Effect of sodium butyrate on primary cultures of adult rat hepatocytes", *In Vitro Cell Dev Biol.*, 23(2):86-92 (Feb. 1987).

Falasca, L., et al., "The effect of retinoic acid on the re-establishment of differentiated hepatocyte phenotype in primary culture", *Cell Tissue Res.*, 293:337-347 (1998).

Germain, L., et al., "Biliary epithelial and hepatocytic cell lineage relationships in embryonic rat liver as determined by the differential expression of cytokeratins, $\alpha$-fetoprotein, albumin, and cell surface-exposed components" *Cancer Res*, 48:4909-4918 (Sep. 1988).

Germain, L., et al., "Promotion of growth and differentiation of rat ductular oval cells in primary culture", *Cancer Res*, 48(2):368-378 (1988).

Gillenwater, A., et al., "Effects of sodium butyrate on growth, differentiation, and apoptosis in head and neck squamous carcinoma cell lines", *Head Neck*, 22(3):247-256 (May 2000).

Gladhaug, I.P., et al., "Effects of butyrate on epidermal growth factor receptor binding, morphology, and DNA synthesis in cultured rate hepatocytes", *Cancer Res*, 48(22):6560-6564 (Nov. 15, 1988).

Graham, K.A., et al., "Sodium butyrate induces differentiation in breast cancer cell lines expressing the estrogen receptor", *J Cell Physiol*, 136(1):63-71 (Jul. 1988).

Grisham, J.W., et al., "Liver stem cells", *Stem Cells*, 233-282 (1997).

Guixiang, T., et al., "Different effects of cyclic AMP and butyrate on eosinophilic differentiation, apoptosis and bcl-2 expression of a human eosinophilic leukemia cell line, EoL-1", *Hematol Oncol*, 14(4):181-92 (Dec. 1996).

Jeng, J.H., et al., "Effects of butyrate and propionate on the adhesion, growth, cell cycle kinetics, and protein synthesis of cultured human gingival fibroblasts", *J Periodontol*, 70(12):1435-1442 (Dec. 1999).

Kamitani, H., et al., "Regulation of 12-lipoxygenase in rat intestinal epithelial cells during differentiation and apoptosis induced by sodium butyrate", *Arch Biochem Biophys*, 368(1):45-55 (Aug. 1, 1999).

Kosugi, H., et al., "Histone deacetylase inhibitors are the potent inducer/enhancer of differentiation in acute myeloid leukemia: a new approach to anti-leukemia therapy", *Leukemia*, 13:1316-1324 (1999).

Lazaro, C.A., et al., "Generation of hepatocytes from oval cell precursors in culture", *Cancer Res*, 58:5514-5522 (Dec. 1, 1998).

Li, J., et al., "Mammalian hepatocyte differentiation requires the transcription factor HNF-4$\alpha$", *Genes & Dev*, 14:464-474 (2000).

Matsui, T., et al., "Induction of catecholamine synthesis in human neuroblastoma cells by replication inhibitors and sodium butyrate", *Brain Res*, 843(1-2):112-117 (Oct. 2, 1999).

McBain, J., et al., "Apoptotic death in adenocarcinoma cell lines induced by butyrate and other histone deacetylase inhibitors", *Biochem Pharm*, 53:1357-1368 (1997).

Michalopoulos, G.K., et al., "Morphogenetic events in mixed cultures of rat hepatocytes and nonparenchymal cells maintained in biological matrices in the presence of hepatocyte growth factor and epidermal growth factor", *Hepatology*, 29(1):90-100 (1999).

Mitaka, T., et al., "Redifferentiation of proliferated rat hepatocytes cultured in L15 medium supplemented with EGF and DMSO", *In Vitro Cell Dev. Biol.*, 29A:714-722 (Sep. 1993).

Mitaka, T., "The current status of primary hepatocyte culture", *Int. J. Exp. Path*, 79:393-409 (1998).

Niki, T., et al., "A histone deacetylase inhibitor, trichostatin A, suppresses myofibroblastic differentiation of rat hepatic stellate cells in primary culture", *Hepatology*, 29(3):858-867 (1999).

Pack, R., et al., "Isolation, biochemical characterization, long-term culture, and pheotype modulation of oval cells from carcinogen-fed rats", *Exp Cell Res*, 204(2):198-209 (1993).

Pagan, R., et al., "Effects of growth and differentiation factors on the epithelial-mesenchymal transistion in cultured neonatal rat hepatocytes", *J of Hepatology*, 31:859-904 (1999).

Perez, R., et al., "Sodium butyrate upregulates Kupffer cell PGE2 production and modulates immune function", *J Surg Res*, 78(1):1-6 (Jul. 15, 1998).

Perrine, SP., et al., "A short-term trial of butyrate to stimulate fetal-globin-gene expression in the beta-globin disorders", *N Engl J Med*, 328(2):81-86, (Jan. 14, 1993).

Perrine, SP., et al., "Butyrate derivatives. New agents for stimulating fetal globin production in the beta-globin disorders", *Am J Pediatr Hemotol Oncol*, 16(1):67-71 (Feb. 1994).

Reynolds, S., et al., "Differentiation-inducing effect of retinoic acid, difluoromethylornithine, sodium butyrate and sodium suramin in human colon cancer cells", *Cancer Lett*, 134(1):53-60 (Dec. 11, 1998).

Rivero JA., et al., "Sodium butyrate stimulates PKC activation and induces differential expression of certain PKC isoforms during erythroid differentiation", *Biochem Biophys Res Commun*, 248(3):664-668 (Jul. 30, 1998).

Rocchi, P., et al., "Effect of butyrate analogues on proliferation and differentiation in human neuroblastoma cell lines", *Anticancer Res*, 18(2A):1099-103 (Mar. 1998).

Rogler, LE., "Selective bipotenital differentiation of mouse embryonic hepatoblasts in vitro", *Am J Pathol*, 150(2):591-602 (1997).

Runge, D., et al., "STAT 1 alpha/1 beta, STAT 3 and STAT 5: Expression and Association with c-MET and EGF-Receptor in Long-Term Cultures of Human Hepatocytes", *Biochemical and Biophysical Research Communications*, 265:376-381 (1999).

Saito, H., et al., "Differentiating effect of sodium butyrate on human hepatoma cell lines PLC/PRF/5, HCC-M and HCC-T", *Int J Cancer*, 48(2):291-296 (May 10, 1991).

Sanchez, A., et al., "Transforming growth factor-B (TGF-B) and EGF promote cord-like structures that indicate terminal differentiation of fetal hepatocytes in primary culture", *Exp Cell Res*, 242:27-37 (1998).

Schultz, RM., et al., "Reprogramming of gene expression during preimplantation development", *J of Exp Zoology (Mol Dev Evol)*, 285:276-282 (1999).

Siavoshian, S., et al., "Butyrate and trichostatin A effects on the proliferation/differentiation of human intestinal epithelial cells: induction of cyclin D3 and p21 expression", *Gut*, 46(4):507-14 (Apr. 2000).

Simon, B., et al., "Transient transcriptional activation of gastrin during sodium butyrate-induced differentiation of islet cells", *Regul Pept*, 70(2-3):143-8 (Jun. 18, 1997).

Staecker, JL., et al., "Stimulation of DNA synthesis in primary cultures of adult rat hepatocytes by sodium butyrate", *Biochem Biophys Res Commun*, 147(1):78-85 (Aug. 1987).

Staecker, JL., et al., "The effect of sodium butyrate on tyrosine aminotransferase induction in primary cultures of normal adult rat hepatocytes", *Arch Biochem Biophys*, 261(2):291-8 (Mar. 1988).

Staecker, JL., et al., "Sodium butyrate preserves aspects of the differentiated phenotype of normal adult rat hepatocytes in culture", *J Cell Physiol*, 135(3):367-76 (1988).

Strain, A., "Ex vivo liver cell morphogenesis: one step nearer to the bioartificial liver", *Hepatology*, 29(1):288-290 (Jan. 1999).

Sun, SH., et al., "Altered phospholipid metabolism in sodium butyrate-induced differentiation of C6 glioma cells", *Lipids*, 32(3):273-82 (Mar. 1997).

Tamagawa, K., et al., "Proanthocyanidins from barley bran potentiate retinoic acid-induced granulocytic and sodium butyrate-induced monocytic differentiation of HL60 cells", *Biosci Biotechnol Biochem*, 62(8):1483-7 (Aug. 1998).

Tanaka, T., et al., "Adenovirus-mediated prodrug gene therapy for carcinoembryonic antigen-producing human gastric carcinoma cells in vitro", *Cancer Res*, 56(6):1341-5 (Mar. 1996).

Tateno, C., et al., "Growth and differentiation of adult rat hepatocytes regulated by the interaction between parenchymal and non-parenchymal liver cells", *J of Gasto and Hepatology*, 13:S83-92 (1998).

Tateno, C., et al., "Growth potential and differentiation capacity of adult rat hepatocytes in vitro", *Wound Repair and Regeneration*, 7(1):36-44 (1999).

Wang, G., et al., "Transforming growth factor-beta 1 acts cooperatively with sodium n-butyrate to induce differentiation of normal human keratinocytes", *Exp Cell Res*, 198(1):27-30 (Jan. 1992).

Watkins, SM., et al., "Butyric acid and tributyrin induce apoptosis in human hepatic tumour cells", *J Dairy Res*, 66(4):559-67 (Nov. 1999).

Yabushita, H., et al., "Effects of sodium butyrate, dimethylsulfoxide and dibutyryl cAMP on the poorly differentiated ovarian adenocarcinoma cell line AMOC-2", *Oncol Res*, 5(4-5):173-82 (1993).

Yamada, K., et al., "Effects of butyrate on cell cycle progression and polyploidization of various types of mammalian cells", *Biosci Biotechnol Biochem*, 56(8):1261-5 (Aug. 1992).

Yoon, J-H., et al., "Augmentation of Urea-synthetic Capacity by Inhibition of Nitric Oxide Synthesis in Butyrate-Induced Differentiated Human Hepatocytes", *FEBS Letters*, 474:175-178 (2000).

Yoon, J-H., et al., "Development of a non-transformed human liver cell line with differentiated-hepatocyte and urea-synthetic functions: applicable for bioartificial liver", *Int. J. of Artificial Organs*, 22:769-777(1999).

Yoshizawa, T., et al., "Dimethylsulfoxide maintains intercellular communication by preserving the gap junctional protein connexin32 in primary cultured hepatocyte doublets from rats", *J of Gastro and Hepat*, 12:325-330 (1997).

Zvibel, I., et al., "Phenotypic characterization of rat hepatoma cell lines and lineage-specific regulation of gene expression by differentiation agents", *Differentiation*, 63:215-223 (1998).

Kaneko et al., Alteration of Differentiation State of Human Hepatocytes Cultured with Novoblocin and Butyrate, Cancer Res 50:3101 (1990).

Kobayashi et al., Establishment of a Highly Differentiated Immortalized Human Hepatocyte Cell Line as a Source of Hepatic Function in the Bioartificial Liver, Transplantation Proceedings 32:237 (2000).

Koutsovelkidis et al., Butyrate Inhibits and Excherichia Coli-Derived Mitogen(s) Stimulated DNA Synthesis in Human Hepatocytes In Vitro, Prep Biochem & Biotechnol 29:121 (1999).

Masuda et al., Up-Regulation of E-Cadherin and β-Catenin in Human Hepatocellular Carcinoma Cell Lines by Sodium Butyrate and Interfereon, In Vitro Cell Dev Biol—Animal 36:387 (2000).

Saito et al., Effect of Dexamethasone, Dimethylsulfoxide and Sodium Butyrate on a Human Hepatoma Cell Line PLC?PRF/5, Cancer Biochem Biophys 13:75 (1992).

Saito et al., Changes of Antigen Expression on Human Hepatoma Cell Lines Caused by Sodium Butyrate, a Differentiation Inducer, J Gastroenterol 29:733 (1994).

Yoon et al., Development of a Non-Transformed Human Liver Cell Line with Differentiated-Hepatocyte and Urea-Synthetic Functions: Applicable for Bioartificial Liver, 22:796 (1999).

Yoon et al., Augmentation of Urea-Synthetic Capacity by Inhibition of Nitric Oxide Synthesis in Butyrate-Induced differentiated Human Hepatocytes, FEBS Letters 474:175 (2000).

Information from the ATCC website.

Information from Webster's Online Dictionary.

* cited by examiner

FBS Alone — FBS + Sodium Butyrate

10X

20X

20X

A

B

PROCESS FOR MAKING HEPATOCYTES FROM PLURIPOTENT STEM CELLS

REFERENCE TO RELATED APPLICATIONS

This application is a continuation-in-part of U.S. Ser. No. 09/718,308, filed Nov. 20, 2001; U.S. Ser. No. 09/872,182, filed May 31, 2001 now U.S. Pat. No. 6,506,571, issued Jan. 14, 2003; and International Patent Application PCT/US01/13471, filed Apr. 26, 2001, designating the U.S., to be published in English 18 months after the first priority date pursuant to Article 21(2) of the PCT. This application also claims priority to U.S. provisional patent application 60/200,095, filed Apr. 27, 2000. The four priority applications and U.S. utility application Ser. No. 09/718,308 are hereby incorporated herein by reference in their entirety.

TECHNICAL FIELD

This invention relates generally to the field of cell biology of embryonic cells and liver cells. More specifically, this invention relates to the directed differentiation of human pluripotent stem cells to cells of the hepatocyte lineage under special culture conditions.

BACKGROUND

Liver disease affects millions of people worldwide. Fulminant hepatic failure is the clinical term for an immediate and catastrophic cessation in liver function, usually leading to death within a matter of hours. Other forms of liver disease, such as chronic hepatitis and cirrhosis, involve an insidious and progressive failure of liver function, with grim effects on physiological well-being and long-term prognosis. In the United States, there are an estimated 300,000 hospitalizations each year for liver disease, and 30,000 deaths—with only about 4,500 donor livers available for transplant.

A healthy liver has a remarkable ability to regenerate itself—but when this ability is compromised, the consequences are dire. An important challenge of modern medicine is to find a way to supplement the natural process of regeneration, and thereby restore liver function to affected patients.

Some early work has been done to identify liver progenitor cells in small animal models. Agelli et al. (Histochem. J. 29:205, 1997), Brill et al. (Dig. Dis. Sci. 44:364, 1999 and), and Reid et al. (U.S. Pat. No. 5,576,207) have proposed expansion conditions for early hepatic progenitor cells from embryonal and neonatal rat livers. Michalopoulos et al. (Hepatology 29:90, 1999) report a system for culturing rat hepatocytes and nonparenchymal cells in biological matrices. Block et al. (J. Cell Biol. 132:1133, 1996) developed conditions for expansion, clonal growth, and specific differentiation in primary cultures of hepatocytes induced by a combination of growth factors in a chemically defined medium. It has been known for some time that mature rat liver cells derive from precursors (sometimes referred to as "hepatoblasts" or "oval cells") that have the capacity to differentiate into either mature hepatocytes or biliary epithelial cells (L. E. Rogler, Am. J. Pathol. 150:591, 1997; M. Alison, Current Opin. Cell Biol. 10:710, 1998; Lazaro et al., Cancer Res. 58:514, 1998; Germain et al., Cancer Res. 48:4909, 1988).

Unfortunately, a ready source of human hepatocytes for reconstitution therapy has not been identified. European Patent Application EP 953 633 A1 proposes a cell culturing method and medium for producing proliferated and differentiated human liver cells, apparently from donated human liver tissue. In most people's hands, the replication capacity of human hepatocytes in culture has been disappointing. As a remedy, it has been proposed that hepatocytes be immortalized by transfecting with large T antigen of the SV40 virus (U.S. Pat. No. 5,869,243).

A number of recent discoveries have raised expectations that stem cells may become a source of a variety of cell types and tissues for replacing those damaged in the course of disease, infection, or from congenital abnormalities. Various types of putative stem cells differentiate as they divide, maturing into cells that can carry out the unique functions of particular tissues, such as the heart, the liver, or the brain.

A particularly important development has been the isolation of two types of human pluripotent stem (hPS) cells from embryonic tissue. Pluripotent cells are believed to have the capacity to differentiate into most cell types in the body (R. A. Pedersen, Scientif. Am. 280(4):68, 1999). Early work on embryonic stem cells was done in mice (reviewed in Robertson, Meth. Cell Biol. 75:173, 1997; and Pedersen, Reprod. Fertil. Dev. 6:543, 1994). However, monkey and human pluripotent cells have proven to be much more fragile, and do not respond to the same culture conditions as mouse embryonic cells. It is only recently that discoveries were made that allow primate embryonic cells to be obtained and cultured ex vivo.

Thomson et al. (U.S. Pat. No. 5,843,780; Proc. Natl. Acad. Sci. USA 92:7844, 1995) were the first to successfully culture embryonic stem cells from primates. They subsequently derived human embryonic stem (hES) cell lines from human blastocysts (Science 282:114, 1998). Gearhart and coworkers derived human embryonic germ (hEG) cell lines from fetal gonadal tissue (Shambloft et al., Proc. Natl. Acad. Sci. USA 95:13726, 1998 and International Patent Application WO 98/43679). Both hES and hEG cells have the long-sought characteristics of human pluripotent stem (hPS) cells: they are capable of ongoing proliferation in vitro without differentiating, they retain a normal karyotype, and they retain the capacity to differentiate to produce all adult cell types.

Spontaneous differentiation of pluripotent stem cells in culture or in teratomas generates cell populations with a heterogeneous mixture of phenotypes, representing a spectrum of different cell lineages. In a number of applications, it is desirable for differentiated cells to be of a more homogeneous nature—both in terms of the phenotypes they express, and in terms of the types of progeny they can generate.

Accordingly, there is a need for technology to generate more homogeneous differentiated cell populations from pluripotent embryonic cells of primate origin, particularly those from humans.

SUMMARY

This invention provides a system for efficient production of primate cells that have differentiated from pluripotent cells into cells of the hepatocyte lineage. Cultures of such cells have been obtained that are relatively enriched for characteristics typical of liver cells, compared with undifferentiated cells and cells that are committed to other tissue types.

One embodiment of the invention is a cell population obtained by differentiating primate pluripotent stem (pPS) cells in such a manner that a significant proportion of cells in the population have characteristics of cells of the hepatocyte lineage. Desirable characteristics are listed later in the description. The cells may demonstrate any or all of the following: antibody-detectable expression of $\alpha_1$-antitrypsin or albumin; absence of antibody-detectable expression of $\alpha$-fetoprotein; expression of asialoglycoprotein receptor at a level detectable by reverse PCR amplification; evidence of glycogen storage; evidence of cytochrome p450 or glucose-6-phosphatase activity; and morphological features of hepatocytes. Preferred cell populations have more of these hepatocyte characteristics in a greater proportion of the cells in the population. It is understood that the cells may replicate to form progeny, both during differentiation, and in subsequent manipulation. Such progeny also fall within the scope of the invention in all instances where not explicitly excluded.

Exemplary cells are obtained by differentiating embryonic stem (hES) cells obtained from cultures that originated from human blastocysts. The differentiated cells are generated by culturing the pPS cells in a growth environment that comprises a hepatocyte differentiation agent, such as n-butyric acid or other differentiation agent outlined in the disclosure. The differentiation agent can be added directly to undifferentiated pPS cells cultured with or without feeder cells. Alternatively, the pPS cells are allowed to differentiate into a mixed cell population (e.g., by forming embryoid bodies or by culture overgrowth), and the differentiation agent is added to the mixed population. What emerges is a less heterogeneous population, in which a substantial proportion of the cells have the desired phenotype. In some instances, the culture method also includes hepatocyte maturation factors such as those exemplified in the disclosure, which include solvents like DMSO, growth factors like FGF, EGF, and hepatocyte growth factor, and glucocorticoids like dexamethazone.

Where derived as progeny from an established line of pPS cells, the cell populations and isolated cells of this invention will typically have the same genome as the line from which they are derived. This means that the chromosomal DNA will be over 90% identical between the pPS cells and the derived cells, which can be inferred if the hepatocyte-like cells are obtained from the undifferentiated line through the course of normal mitotic division. Hepatocyte-like cells that have been treated by recombinant methods to introduce a transgene (such as TERT) or knock out an endogenous gene are still considered to have the same genome as the line from which they are derived, since all non-manipulated genetic elements are preserved.

Another embodiment of the invention is a differentiated cell having characteristics of a cell of the hepatocyte lineage, which is either harvested from a differentiated cell population of this invention, or is the progeny of a cell harvested from such a population. Exemplary is a differentiated cell produced by providing a human pluripotent stem (hPS) cells in a growth environment essentially free of feeder cells; culturing the hPS cells in a medium containing a hepatocyte differentiation agent under conditions that produce a cell population enriched for cells with characteristic features of hepatocytes; and subsequently harvesting the differentiated cell from the enriched cell population.

Another embodiment of the invention is a method of treating human pluripotent stem (hPS) cells to obtain differentiated cells that can be maintained in an in vitro culture, by providing a culture of the hPS cells, and culturing the cells on a substrate in a culture medium containing a hepatocyte differentiation agent under conditions that permit enrichment of the differentiated cells. Beneficial techniques and reagents for use in the context of such methods are detailed later in the disclosure. Also embodied in the invention is a differentiated cell produced according to a method of this invention, particularly those having characteristics of cells of the hepatocyte lineage.

Yet another embodiment of the invention is a method of screening a compound for hepatocellular toxicity or modulation, comprising contacting a differentiated cell of this invention, and determining any phenotypic or metabolic changes in the cell that result. Another embodiment of the invention is a method of detoxifying a fluid such as blood, comprising contacting a differentiated cell of this invention with the fluid under conditions that permit the cell to remove or modify a toxin in the fluid. In this context, the differentiated cells described in this disclosure can be used as part of a liver support device, or for therapeutic administration for reconstituting hepatocellular function in an individual.

These and other embodiments of the invention will be apparent from the description that follows.

DRAWINGS

FIG. 1 is a half-tone reproduction of a phase contrast photomicrograph (4×, 10×, 20×). Right side: Embryoid body cells from human pluripotent embryonic stem (hES) cells were cultured for 2 days in the hepatocyte differentiating agent n-butyrate. The resulting cells show homogenous morphology. Left side: Embryoid body cells cultured in serum (FBS) containing medium alone. There are heterogeneous patches of cells that show the morphology of many different cell types.

Figure 2:
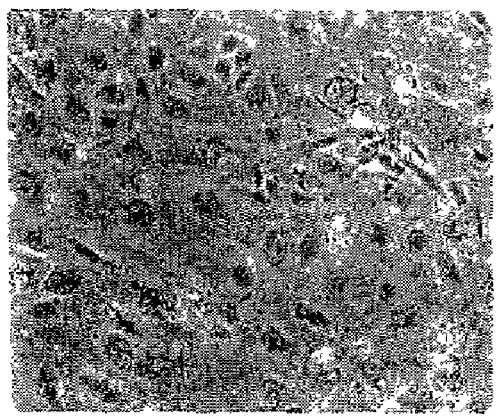
Figure 2:
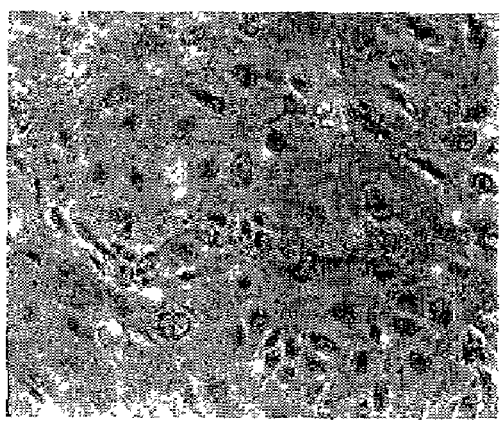
Figure 2:
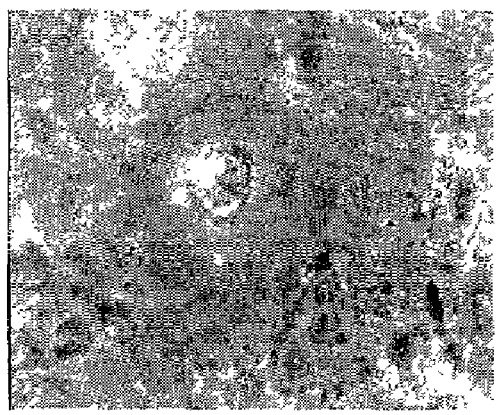
Figure 2:
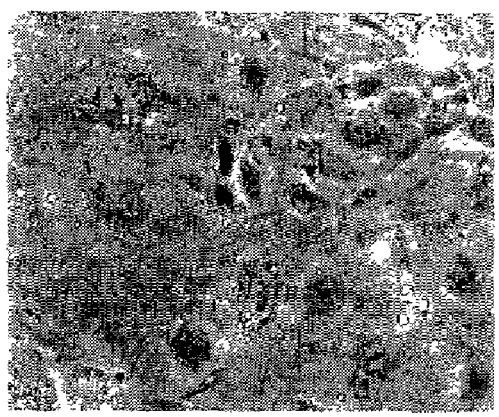
Figure 2:
Figure 2:
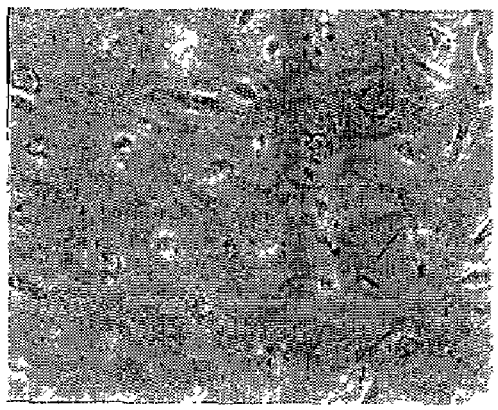

FIG. 2 is a half-tone reproduction of a phase contrast photomicrograph (10× in the upper two panels, 20× in the other panels). These are cells that have been differentiated by culturing 6 days with n-butyrate. The cells predominantly demonstrate characteristics of mature hepatocytes. The cells in this field are binucleated and polygonal in shape, and express markers of mature hepatocytes detectable by immunostaining or reverse PCR.

Figure 3A:
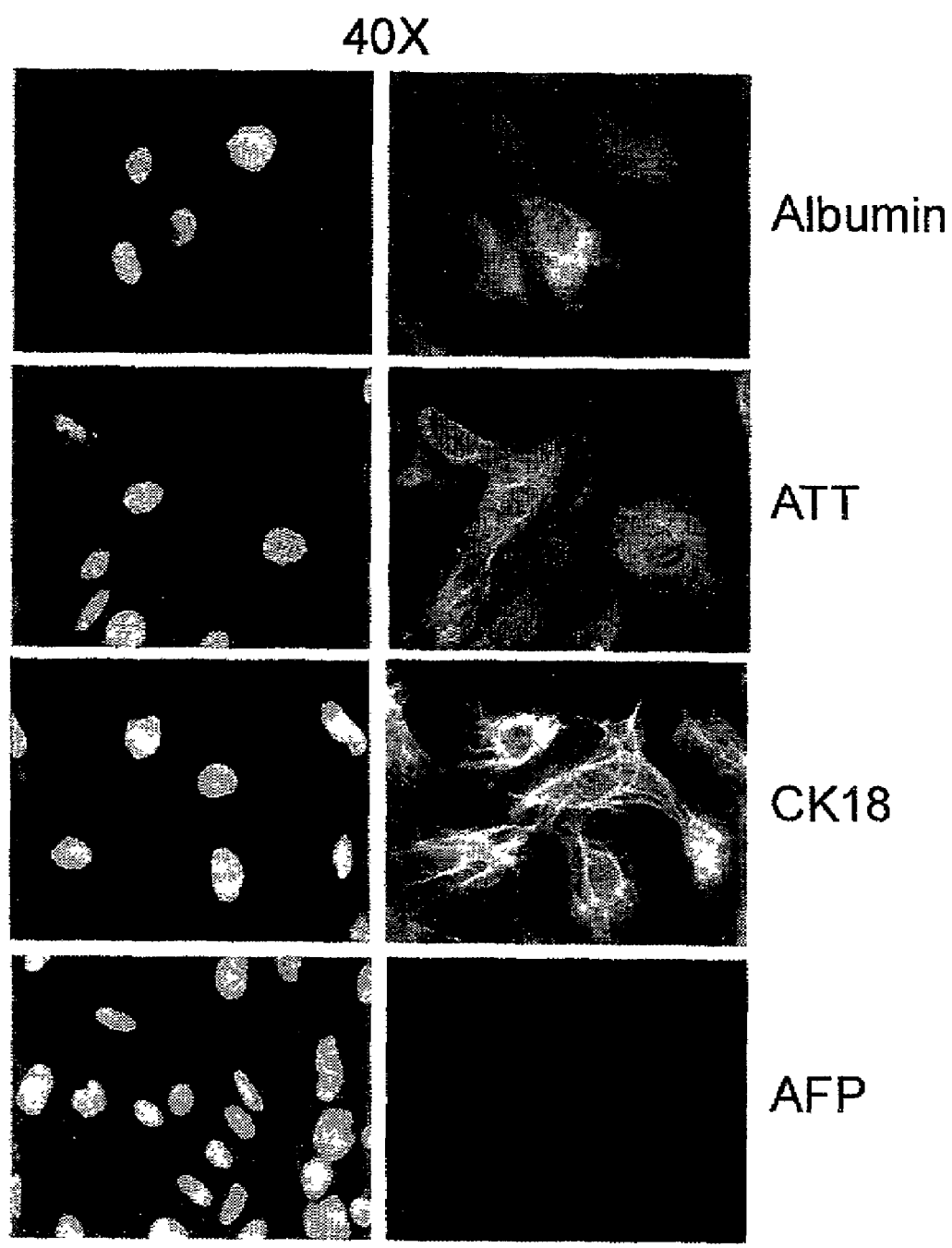
Figure 3B:
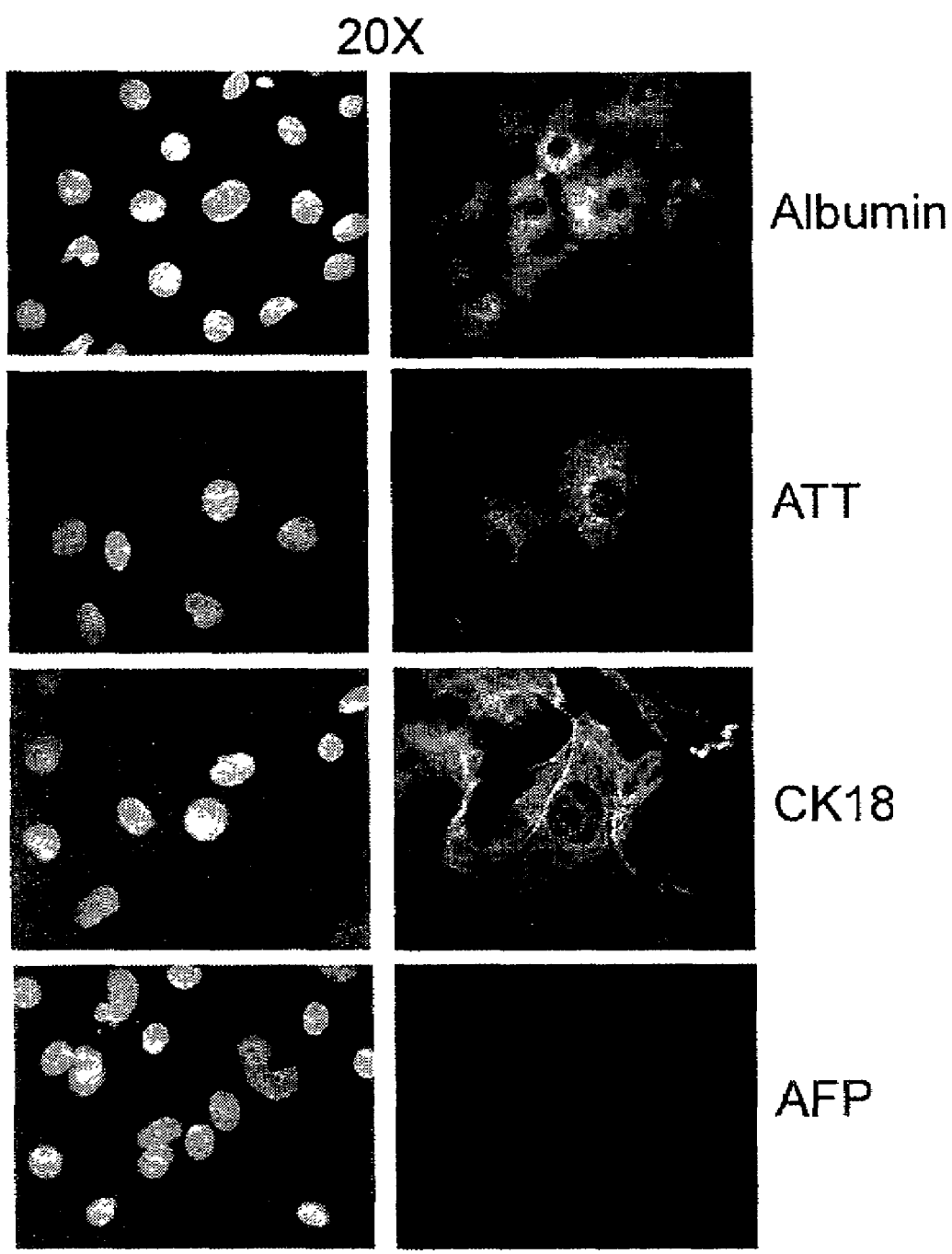

FIG. 3 is a half-tone reproduction showing the results of immunohistochemical staining for certain cell specific markers (right side), compared with the position of cell nuclei in the same field (bisbenzimide staining, left side). FIG. 3A (40×) shows the results for adult human hepatocytes; FIG. 3B (20×) shows the results for hES cells differentiated by culturing 6 days with n-butyrate. Both cultures show a high proportion of cells staining positive for albumin, $\alpha_1$-antitrypsin, and CD18, (three markers characteristic of cells of the hepatocyte lineage), and negative for $\alpha$-fetoprotein (a marker of less mature cells).

Figure 4:
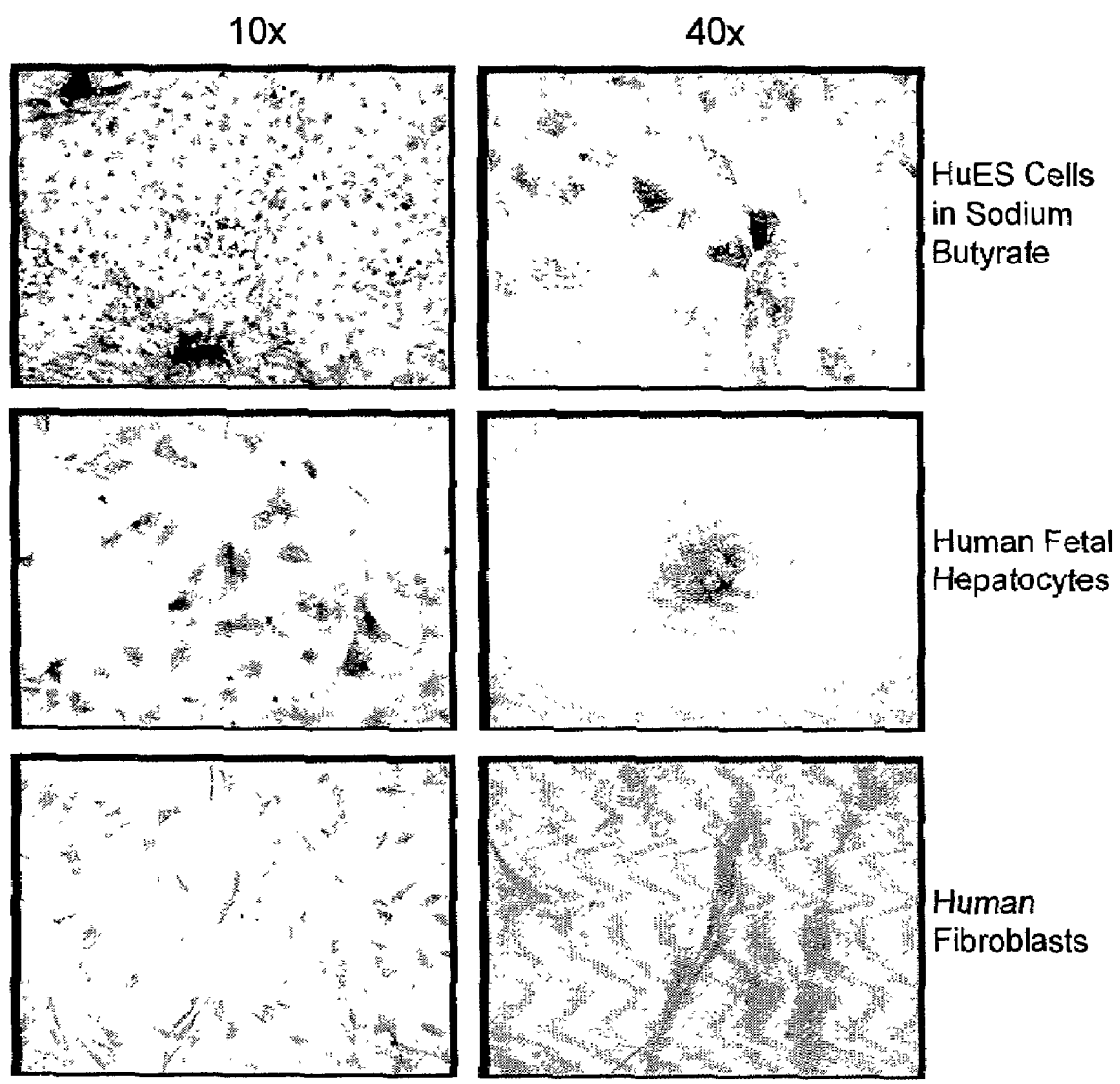

FIG. 4 is a half-tone reproduction of cells stained with Periodic Acid Schiff for the presence of glycogen (10× and 40×). ~60% of the butyrate treated cells (top row) show evidence of glycogen storage, compared with ~80% in fetal hepatocytes (middle row) and virtually none in the fibroblast cell line (bottom row).

Figure 5:
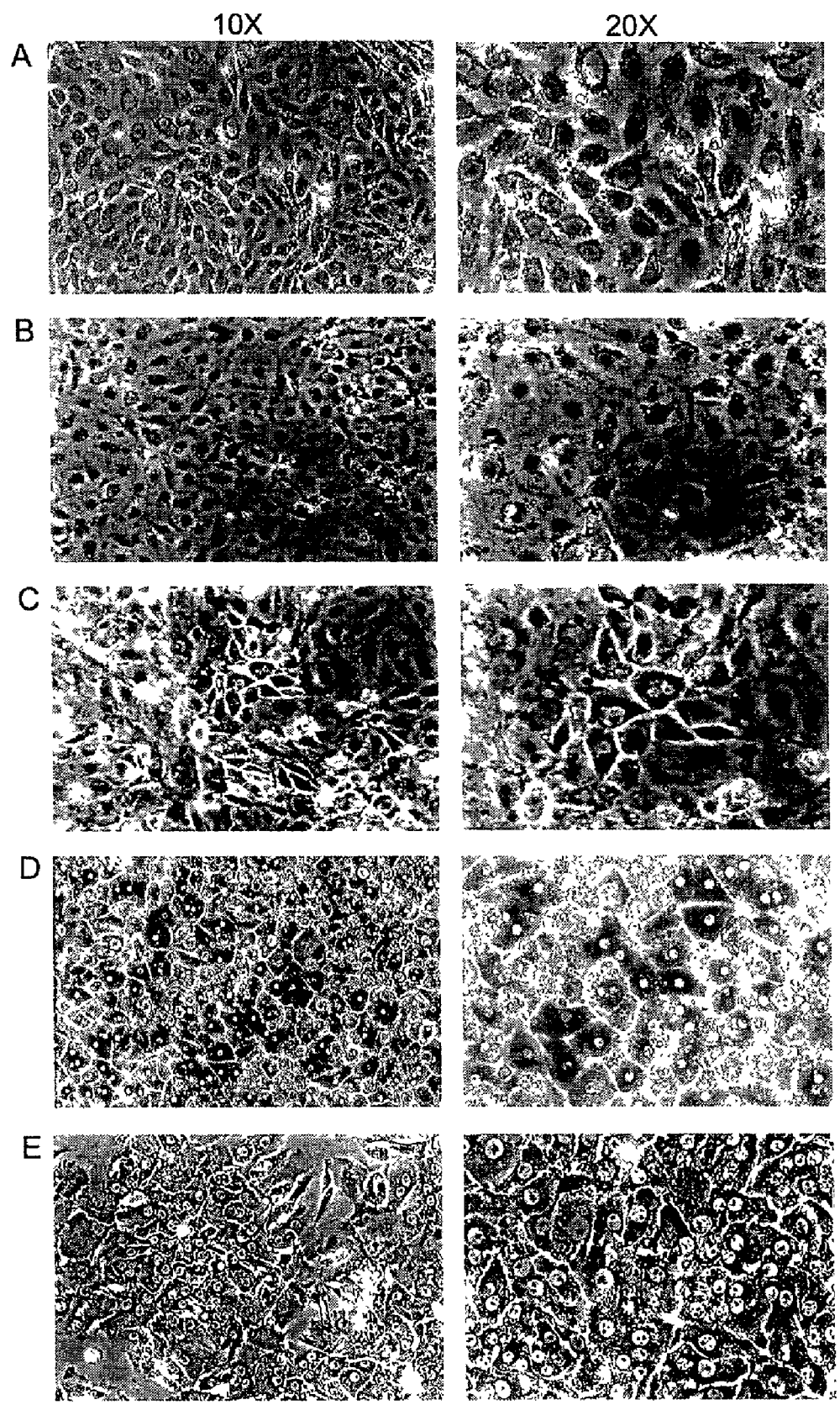

FIG. 5 is a half-tone reproduction of a phase contrast photomicrograph (10×, 40×), showing cells at various times during an exemplary differentiation and maturation process. Row A shows cells 4 days after culture in SR medium containing 5 mM sodium n-butyrate. More than 80% of cells in the culture are large in diameter, containing large nuclei and granular cytoplasm. After 5 days, the cells were switched to specialized hepatocyte culture medium (HCM). Rows B and C show the appearance after culturing in HCM for 2 or 4 days. Multinucleated polygonal cells are common. By these criteria, the ES-derived cells resemble freshly isolated human adult hepatocytes (Row D) and fetal hepatocytes (Row E).

Figure 6:
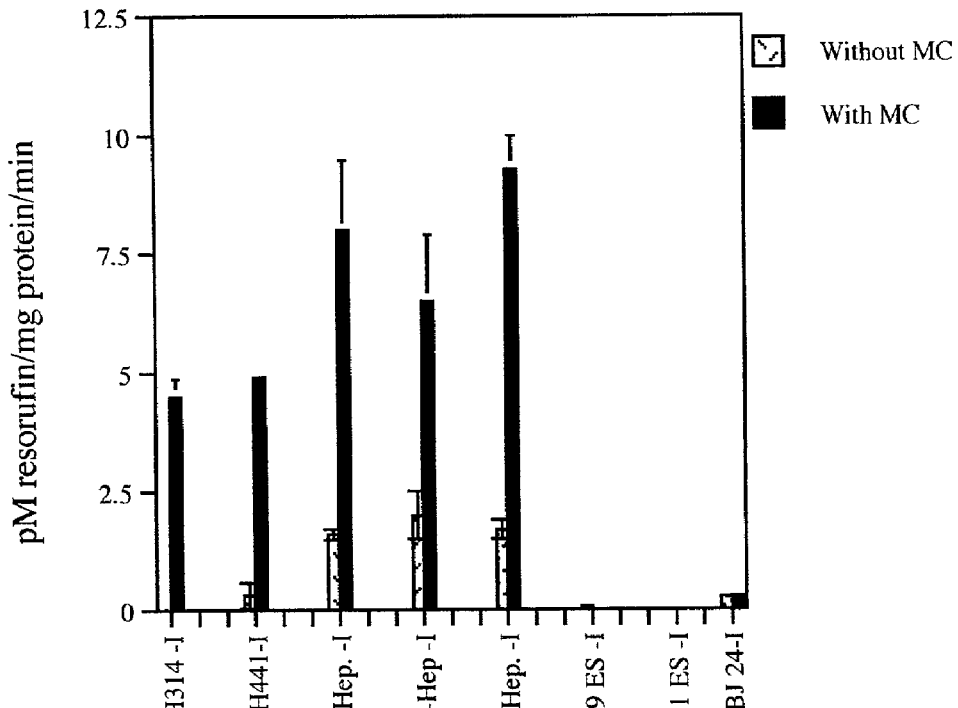
Figure 6:
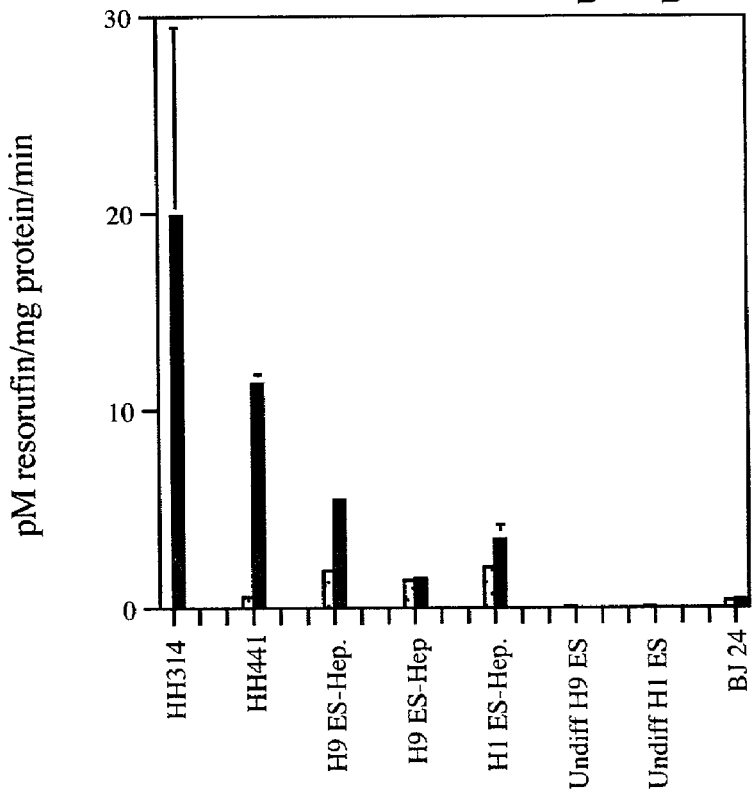

FIG. 6 is a bar graph, showing activity of cytochrome P-450 enzymes 1A1 and 1A2 (CYP1A1/2). The enzyme was induced by culturing with 5 μM methylchloranthrene (MC), and then measured using ethoxyresorufin. CYP1A1/2 activity was detected in two hepatocyte lineage lines derived from the H1 line of ES cells, and one derived from the H9 line. The level of activity exceeded the level observed in two preparations of freshly isolated human adult hepatocytes (HH). Activity in undifferentiated H1 and H9 cells and BJ embryonic fibroblasts was negligible.

DETAILED DESCRIPTION

This invention provides a system for preparing differentiated cells of the hepatocyte lineage from the pluripotent stem cells of primate origin.

It has been discovered that when pluripotent stem cells are cultured in the presence of a hepatocyte differentiation agent, a population of cells is derived that has a remarkably high proportion of cells with phenotypic characteristics of cultured liver cells. Optionally, the effect can be enhanced by also culturing the cells in the presence of a hepatocyte maturation factor. Since pluripotent stem cells can proliferate in culture for a year or more (over 300 population doublings), the invention described in this disclosure provides an almost limitless supply of hepatocyte-like cells, suitable for a variety of developmental and therapeutic purposes.

FIG. 2 shows phase contrast photomicrographs of cells that have been differentiated by culturing with a prototype hepatocyte differentiation agent, n-butyrate. The cells show uniform features of hepatocytes, including a polygonal shape, and display characteristic phenotypic markers such as albumin, $\alpha_1$-antitrypsin (AAT), and the asialoglycoprotein receptor, while lacking α-fetoprotein. The cells have been maintained in butyrate-containing medium for periods of 1-3 weeks.

The discovery is surprising, in view of the fact that histone deacetylase inhibitors like butyrate and trichostatin A have been implicated in the differentiation of a wide variety of cell types. A priori, it would be logical to predict that butyrate would drive pluripotent stem cell populations to differentiate into a widely heterogeneous population, such as results from growing embryonic stem cells without feeders, or in the presence of retanoic acid. Contrary to this prediction, a remarkably homogeneous population of hepatocyte lineage cells is obtained.

This represents an important new paradigm in differentiation of human pluripotent stem cell populations. To our knowledge, there have been no public reports of such a uniform population of hepatocyte lineage cells being obtained from any type of embryonic stem cell.

The effects of butyrate on DNA synthesis and marker expression in primary hepatocyte cultures have been studied by Gladhaug et al. (Cancer Res. 48:6560, 1988), Engelmann et al. (In vitro Cell. Dev. Biol. 23:86, 1987), Staecker et al. (J. Physiol. 135:367, 1988; Arch. Biochem. Biophys. 261: 291, 1988; and Biochem. Biophys. Res. Commun. 147:78, 1987). The effects of butyrate on human liver cell lines has been studied by Saito et al. (Int. J. Cancer 48:291, 1991) and Yoon et al. (Int. J. Artif. Organs 22:769, 1999). The effects of butyrate on rat oval cells (a hepatocyte precursor) have been studied by Pack et al. (Exp. Cell Res. 204:198, 1993), and Germain et al. (Cancer Res. 48:368, 1988). The effect of Trichostatin A on rat hepatic stellate cells in primary culture was studied by Niki et al. (Hepatology 29:858, 1999; and European Patent Application EP 9837742 A1). The effect of butyrate on embryonic rat liver epithelial cells bipotential for hepatocytes and biliary epithelium was studied by Blouin et al. (Exp. Cell Res. 21:22, 1995). The effect of butyrate on cultured rat liver epithelial cell precursors was studied by Coleman et al. (J. Cell. Physiol. 161:463, 1994). L. E. Rogler (Am. J. Pathol. 150:591, 1997) reported that treatment of a mouse hepatoblast cell line with DMSO or sodium butyrate induced rapid hepatocytic differentiation. Watkins et al. (J. Dairy Res. 66:559, 1999) report that butyric acid can also induce apoptosis in human hepatic tumor cells. All these studies relate to cells that are mature hepatocytes, either transformed liver cells, or committed hepatocyte precursor cells.

Butyrate has been shown to have a differentiating and modulating effect on a variety of other cell types, both in culture and in vivo. Kosugi et al. (Leukemia 13:1316, 1999) and Tamagawa (Biosci. Biotechnol. Biochem. 62:1483, 1998) report that histone deacetylase inhibitors are potent inducers of differentiation in acute myeloid leukemia cells. Davis et al. (Biochem J. 346 pt 2:455, 2000) and Rivero et al. (Biochem. Biophys. Res. Commun. 248:664, 1998) discuss the effect of butyrate in erythroblastic differentiation. Perrine et al. (Am. J. Pediatr. Hematol. Oncol. 16:67, 1994) and Perrine et al. (N. Engl. J. Med. 328:81, 1993 have proposed butyrate derivatives as agents for stimulating fetal globin production in beta-globin disorders. Tai et al. (Hematol. Oncol. 14:181, 1996) analyze the effect of butyrate differentiation of eosinophilic granule-containing cells.

U.S. Pat. No. 5,763,255 report methods for inducing differentiation of epithelial cells, in which 5 mM butyric acid is added to undifferentiated cells on a dried native fibrillar collagen cell culture substrate. Yamada et al. (Biosci. Biotech. Biochem. 56:1261, 1992) studied the effects of butyrate on three fibroblast and two epithelial cell lines. Jeng et al. (J. Periodontal. 70:1435, 1999) studied the effects of butyrate and propionate on cultured gingival fibroblasts. Devereux et al. (Cancer Res. 59:6087, 1999) reported that treatment of a human fibroblast cell line with trichostatin A induced the cells to express telomerase reverse transcriptase. Yabushita et al. (Oncol. Res. 5:173, 1993) studied the effects of butyrate, DMSO and dibutyryl cAMP on ovarian adenocarcinoma cells. Graham et al. (J. Cellular Physiol. 136:63, 1988) report that sodium butyrate induces differentiation of breast cancer cell lines. Kamitani (Arch. Biochem. Biophys. 368:45, 1999), Siavoshian et al. (Gut 46:507, 2000), and Reynolds et al. (Cancer Left. 11:53, 1998) studied the effect of sodium butyrate and trichostatin A on the proliferation and differentiation of human intestinal epithelial cells and colon cancer cells. McBain et al. (Biochem. Pharmacol. 53:1357, 1997) report that apoptotic death in adenocarcinoma cell lines can be induced by butyrate and other histone deacetylase inhibitors.

Rocchi et al. (Anticancer Res. 18:1099, 1998) and Matsui et al. (Brain Res. 843:112, 1999) report the effect of butyrate analogues on proliferation, differentiation, and induction of catecholamine synthesis in human neuroblastoma cells. Gillenwater et al. (Head Neck 2:247, 2000) studied the effects of sodium butyrate on squamous carcinoma cell lines. Buommino et al. (J. Mol. Endocrinol.) studied the effect of butyrate on cell differentiation of seminal vesicle epithelial cells. Sun et al. (Lipids 32:273, 1997) studied butyrate-induced differentiation of glioma cells. Wang et al. (Exp. Cell. Res. 198:27, 1992) studied the effect of n-butyrate in differentiating normal human keratinocytes. Perez et al. (J. Surg. Res. 78:1, 1998) report that butyrate upregulates PGE2 production by Kupffer cells and modulates immune function. Schultz et al. (J. Exp. Zool. (Mol. Dev. Evol.) 285:276, 1999) found that treatment of 2-cell embryos with histone deacetylase inhibitors reprogrammed expression of certain genes. Chen et al. (Proc. Natl. Acad. Sci. 94:5798, 1997 and PCT application WO 97/47307) report the use of histone deacetylase inhibitors for reactivating virally transduced genes. Simon et al. (Regul. Pept. 70:143, 1997) studied the effects of butyrate on inducing differentiation of pancreatic islet cells, resulting in an increase in insulin production.

Because butyrate and related compounds promote differentiation in such a large number of different cell types, one would expect a priori that treating a mixed cell population derived from pluripotent embryonic cells would cause each cell in the population to differentiate further along the line to which it is already committed—resulting simply in a more mature mixed cell population. It could not have been predicted that butyrate treatment would result in a uniform cell population—or what tissue type such cells would become.

This invention relates to the surprising discovery that culturing embryonic pluripotent cells with butyrate (or another hepatocyte differentiation factor, detailed below) produces a population of cells that has a remarkably high proportion of cells with phenotypic characteristics of liver cells.

A frequent consequence of culturing pluripotent cells with the differentiation factors is that over 80% of cells are lost from the culture in the first 24 hours. What emerges after several days in culture is a population predominated by cells having characteristic features of the hepatocyte lineage—such as a polygonal binucleated phenotype, markers such as $\alpha_1$-antitrypsin, and albumin, and expression of metabolically important enzyme activity, such as the cytochrome p450 enzymes1A1 and 1A2. While not implying any limitation on the practice of the invention, it is hypothesized that butyrate and other differentiation factors either help induce cells to commit to the hepatocyte lineage—or preferentially promote survival of cells of the hepatocyte lineage—or have a combination of both these effects.

What follows is a further description of how this culture system can be employed to generate hepatocyte lineage cells from pluripotent embryonic stem cells of primate origin. The use of hepatocyte differentiation agents (exemplified by but not limited to n-butyrate) is described, along with other features of the culture system that promote generation of hepatocyte lineage cells in culture.

Since pluripotent embryonic stem cells can essentially be grown indefinitely, this system provides an unbounded supply of hepatocyte-like cells for use in research, pharmaceutical development, and the therapeutic management of liver disease.

Definitions

The terms "hepatocyte lineage" cell, "hepatoblastoid" cell and "hepatoembryoid" cell may be used in reference to the differentiated cells of this invention, obtained by differentiating pluripotent cells in the manner described. The differentiated cells have at least one of a variety of distinguishing phenotypic characteristics of known hepatocyte precursor cells, hepatoblasts, and hepatocytes, as provided later in this disclosure. By the use of these terms, no particular limitation is implied with respect to cell phenotype, cellular markers, cell function, or proliferative capacity, except where explicitly required.

A "hepatocyte precursor cell" or a "hepatocyte stem cell" is a cell that can proliferate and further differentiate into a hepatocyte, under suitable environmental conditions. Such cells may on occasion have the capacity to produce other types of progeny, such as oval cells, bile duct epithelial cells, or additional hepatocyte precursor cells.

"Hepatocyte differentiation agent" and "hepatocyte maturation factor" are two terms with different meanings used in this disclosure to represent a collection of compounds that can be used in preparing and maintaining the differentiated cells of this invention. These agents are further described and exemplified in the sections that follow. The terms are not meant to imply a particular mode or timing of action, and no such limitation should be inferred. A "hepatocyte proliferative factor" is a biological or synthetic compound (a peptide, oligosaccharide, or the like) that promotes the proliferation of hepatocytes and/or hepatocyte precursor cells.

Prototype "primate Pluripotent Stem cells" (pPS cells) are pluripotent cells derived from pre-embryonic, embryonic, or fetal tissue at any time after fertilization, and have the characteristic of being capable under the right conditions of producing progeny of several different cell types. As defined for the purposes of this disclosure, pPS cells are capable of producing progeny that are derivatives of all of the three germinal layers: endoderm, mesoderm, and ectoderm, according to a standard art-accepted test, such as the ability to form a teratoma in a suitable host.

Non-limiting exemplars of pPS cells are human embryonic stem (hES) cells, as described by Thomson et al., Science 282:1145, 1998; embryonic stem cells from other primates, such as Rhesus stem cells described by Thomson et al., Proc. Natl. Acad. Sci. USA 92:7844, 1995; and human embryonic germ (hEG) cells, described in Shambloft et al., Proc. Natl. Acad. Sci. USA 95:13726, 1998. Other types of non-malignant pluripotent cells are also included in the term. Specifically, any cells of primate origin that are fully pluripotent (capable of producing progeny that are derivatives of all three germinal layers) are included, regardless of whether they were derived from embryonic tissue, fetal tissue, or other sources.

pPS cell cultures are said to be "essentially undifferentiated" when they display the morphology that clearly distinguishes them from differentiated cells of embryo or adult origin. pPS cells typically have high nuclear/cytoplasmic ratios, prominent nucleoli, and compact colony formation with poorly discernable cell junctions, and are easily recognized by those skilled in the art. Colonies of undifferentiated cells can be surrounded by neighboring cells that are differentiated. Nevertheless, the essentially undifferentiated colony will persist when cultured under appropriate conditions, and undifferentiated cells constitute a prominent proportion of cells proliferating upon passaging of the cultured cells. Cell populations that contain any proportion of undifferentiated pPS with these criteria can be used in this invention. Cell cultures described as essentially undifferentiated will typically contain at least about 20%, 40%, 60%, or 80% undifferentiated pPS, in order of increasing preference.

"Feeder cells" or "feeders" are terms used to describe cells of one type that are co-cultured with cells of a second type, to provide an environment in which the cells of the second type can be maintained, and perhaps proliferate. The feeder cells are optionally from a different species as the cells they are supporting. For example, certain pPS cells can be supported by mouse embryonic fibroblasts (from primary culture or a telomerized line) or human fibroblast-like or mesenchymal cells (such as can be differentiated and selected from hES cells). Typically (but not necessarily), feeder cells are inactivated by irradiation or treatment with an anti-mitotic agent such as mitomycin C, to prevent them from outgrowing the cells they are supporting.

pPS cell populations are said to be "essentially free" of feeder cells if the cells have been passaged to a new culture environment without adding fresh feeder cells. It is recognized that if a previous culture containing feeder cells is used as a source of pPS for passaging, there will be some feeder cells that survive the passage. For example, hES cells are often cultured in a 9.6 cm² well on a surface of ~375,000 primary irradiated embryonic fibroblasts near confluence. At the time of the next passage, perhaps 150,000 feeder cells are still viable, and will be split and passaged along with hES that have proliferated to a number of ~1 to 1.5 million. After a 1:6 split, the hES cells generally resume proliferation, but the fibroblasts will not grow and only a small proportion will be viable by the end of ~6 days of culture. This culture is "essentially free" of feeder cells, with compositions containing less than about 5%, 1%, and 0.2% feeder cells being increasingly more preferred.

A "growth environment" is an environment in which cells of interest will proliferate in vitro. Features of the environment include the medium in which the cells are cultured, the temperature, the partial pressure of $O_2$ and $CO_2$, and a supporting structure (such as a substrate on a solid surface) if present.

A "nutrient medium" is a medium for culturing cells containing nutrients that promote proliferation. The nutrient medium may contain any of the following in an appropriate combination: isotonic saline, buffer, amino acids, antibiotics, serum or serum replacement, and exogenously added factors.

A "conditioned medium" is prepared by culturing a first population of cells in a medium, and then harvesting the medium. The conditioned medium (along with anything secreted into the medium by the cells) may then be used to support the growth of a second population of cells.

The term "antibody" as used in this disclosure refers to both polyclonal and monoclonal antibody. The ambit of the term deliberately encompasses not only intact immunoglobulin molecules, but also such fragments and derivatives of immunoglobulin molecules (such as single chain Fv constructs, diabodies, and fusion constructs) as may be prepared by techniques known in the art, and retaining a desired antibody binding specificity.

"Restricted developmental lineage cells" are cells derived from embryonic tissue, typically by differentiation of pPS cells. These cells are capable of proliferating and may be able to differentiate into several different cell types, but the range of phenotypes of their progeny is limited. Examples include: hematopoetic cells, which are pluripotent for blood cell types; neural precursors, which can generate glial cell precursors that progress to oligodendrocytes; neuronal restrictive cells, which progress to various types of neurons; and hepatocyte progenitors, which are pluripotent for hepatocytes and sometimes other liver cells, such as bile duct epithelium.

General Techniques

For further elaboration of general techniques useful in the practice of this invention, the practitioner can refer to standard textbooks and reviews in cell biology, tissue culture, and embryology. Included are Teratocarcinomas and embryonic stem cells: A practical approach (E. J. Robertson, ed., IRL Press Ltd. 1987); *Guide to Techniques in Mouse Development* (P. M. Wasserman et al. eds., Academic Press 1993); *Embryonic Stem Cell Differentiation in Vitro* (M. V. Wiles, Meth. Enzymol. 225:900, 1993); *Properties and uses of Embryonic Stem Cells: Prospects for Application to Human Biology and Gene Therapy* (P. D. Rathjen et al., Reprod. Fertil. Dev. 10:31, 1998). General information and methodology relating to cells of hepatocyte lineage is found in *Liver Stem Cells* (S. Sell & Z. Ilic, R. G. Landes Co., 1997), in *Stem cell biology* . . . (L. M. Reid, Curr. Opinion Cell Biol. 2:121,1990), and in *Liver Stem Cells* (J. W. Grisham, pp 232-282 in Stem Cells, Academic Press, 1997). Use of hepatocyte-like cells in pharmaceutical research is described in In vitro *Methods in Pharmaceutical Research* (Academic Press, 1997).

Methods in molecular genetics and genetic engineering are described in *Molecular Cloning: A Laboratory Manual*, 2nd Ed. (Sambrook et al., 1989); *Oligonucleotide Synthesis* (M. J. Gait, ed., 1984); *Animal Cell Culture* (R. I. Freshney, ed., 1987); the series *Methods in Enzymology* (Academic Press, Inc.); *Gene Transfer Vectors for Mammalian Cells* (J. M. Miller & M. P. Calos, eds., 1987); *Current Protocols in Molecular Biology and Short Protocols in Molecular Biology*, 3rd Edition (F. M. Ausubel et al., eds., 1987 & 1995); and *Recombinant DNA Methodology II* (R. Wu ed., Academic Press 1995). Reagents, cloning vectors, and kits for genetic manipulation referred to in this disclosure are available from commercial vendors such as BioRad, Stratagene, Invitrogen, ClonTech, and Sigma Chemical Co.

General techniques used in raising, purifying and modifying antibodies, and the design and execution of immunoassays including immunohistochemistry, the reader is referred to *Handbook of Experimental Immunology* (D. M. Weir & C. C. Blackwell, eds.); Current Protocols in Immunology (J. E. Coligan et al., eds., 1991); and R. Masseyeff, W. H. Albert, and N. A. Staines, eds., *Methods of Immunological Analysis* (Weinheim: VCH Verlags GmbH, 1993).

Media and Feeder Cells

Media for isolating and propagating pPS cells can have any of several different formulas, as long as the cells obtained have the desired characteristics, and can be propagated further. Suitable sources are as follows: Dulbecco's modified Eagle's medium (DMEM), Gibco #11965-092; Knockout Dulbecco's modified Eagle's medium (KO DMEM), Gibco #10829-018; 200 mM L-glutamine, Gibco #15039-027; non-essential amino acid solution, Gibco 11140-050; β-mercaptoethanol, Sigma #M7522; human recombinant basic fibroblast growth factor (bFGF), Gibco #13256-029. Exemplary serum-containing ES medium is made with 80% DMEM (typically KO DMEM), 20% defined fetal bovine serum (FBS) not heat inactivated, 1% non-essential amino acids, 1 mM L-glutamine, and 0.1 mM β-mercaptoethanol. Serum-free ES medium is made with 80% KO DMEM, 20% serum replacement, 1% non-essential amino acids, 1 mM L-glutamine, and 0.1 mM β-mercaptoethanol. Not all serum replacements work, an effective serum replacement is Gibco #10828-028. Information on serum free media in the propagation of pluripotent stem cells is published in International Patent Publications WO 97/47734 (Pedersen, U. California) and WO 98/30679 (Price et al., Life Technologies). The medium is filtered and stored at 4° C. for no longer than 2 weeks. Just before use, human bFGF is added to a final concentration of 4 ng/mL (Bodnar et al., Geron Corporation, International Patent Publication WO 99/20741).

pPS cells are typically cultured on a layer of feeder cells that support the pPS cells in various ways, such as the production of soluble factors that promote pPS cell survival or proliferation, or inhibit differentiation. Feeder cells are typically fibroblast type cells, often derived from embryonic or fetal tissue. A frequently used source of feeder fibroblasts is mouse embryo. The feeder cells are plated to near confluence, irradiated to prevent proliferation, and used to support pPS cell cultures.

In an illustration of culturing pPS cells on feeder layers, mouse embryonic fibroblasts (mEF) are obtained from outbred CF1 mice (obtained from SASCO) or other suitable strains. The abdomen of a mouse at 13 days of pregnancy is swabbed with 70% ethanol, and the decidua is removed into phosphate buffered saline (PBS). Embryos are harvested; placenta, membranes, and soft tissues are removed; and the carcasses are washed twice in PBS. They are then transferred to fresh 10 cm culture dishes containing 2 mL trypsin/EDTA, and finely minced. After incubating 5 min at 37° C., the trypsin is inactivated with 5 mL DMEM containing 10% fetal bovine serum (FBS), and the mixture is transferred to a 15 mL conical tube and dissociated. Debris is allowed to settle for 2 min, the supernatant is made up to a final volume of 10 mL, and plated onto a 10 cm tissue culture plate or T75 flask. The flask is incubated undisturbed for 24 h, after which the medium is replaced. When flasks are confluent (~1-2 d), the cells are split 1:2 into new flasks.

Feeder cells are propagated in mEF medium, containing 90% DMEM (Gibco #11965-092), 10% FBS (Hyclone #30071-03), and 2 mM glutamine. mEF are propagated in T150 flasks (Corning #430825), splitting the cells 1:2 every other day with trypsin, keeping the cells subconfluent, and optionally frozen when necessary. To prepare the feeder cell layer, cells are irradiated at a dose to inhibit proliferation but permit synthesis of important factors that support hES cells (~4000 rads gamma irradiation). Six-well culture plates (such as Falcon #304) are coated by incubation at 37° C. with 1 mL 0.5% gelatin per well overnight, and plated with 375,000 irradiated mEF per well. Feeder cell layers are used 5 h to 1 week after plating. The medium is replaced with fresh hES medium just before seeding pPS cells.

Preparation of Primate Pluripotent Stem (pPS) Cells

Embryonic stem cells can be isolated from blastocysts of members of the primate species (Thomson et al., Proc. Natl. Acad. Sci. USA 92:7844, 1995). Human embryonic stem (hES) cells can be prepared from human blastocyst cells using the techniques described by Thomson et al. (U.S. Pat. No. 5,843,780; Science 282:1145, 1998; Curr. Top. Dev. Biol. 38:133 ff., 1998).

To obtain human blastocysts, human in vivo preimplantation embryos or in vitro fertilized (IVF) embryos can be used or one cell human embryos can be expanded to the blastocyst stage (Bongso et al., Hum Reprod 4: 706, 1989). Briefly, human embryos are cultured to the blastocyst stage in G1.2 and G2.2 medium (Gardner et al., Fertil. Steril. 69:84, 1998). Blastocysts that develop are selected for ES cell isolation. The zona pellucida is removed from blastocysts by brief exposure to pronase (Sigma). The inner cell masses are isolated by immunosurgery, in which blastocysts are exposed to a 1:50 dilution of rabbit anti-human spleen cell antiserum for 30 minutes, then washed for 5 minutes three times in DMEM, and exposed to a 1:5 dilution of Guinea pig complement (Gibco) for 3 minutes (see Solter et al., Proc. Natl. Acad. Sci. USA 72:5099, 1975). After two further washes in DMEM, lysed trophectoderm cells are removed from the intact inner cell mass (ICM) by gentle pipetting, and the ICM plated on mEF.

After 9 to 15 days, inner cell mass-derived outgrowths are dissociated into clumps either by exposure to calcium and magnesium-free phosphate-buffered saline (PBS) with 1 mM EDTA, by exposure to dispase or trypsin, or by mechanical dissociation with a micropipette; and then replated on mEF in fresh medium. Dissociated cells are replated on embryonic feeder layers in fresh ES medium, and observed for colony formation. Colonies demonstrating undifferentiated morphology are individually selected by micropipette, mechanically dissociated into clumps, and replated. ES-like morphology is characterized as compact colonies with a high nucleus to cytoplasm ratio and prominent nucleoli.

Human Embryonic Germ (hEG) cells can be prepared from primordial germ cells present in human fetal material taken about 8-11 weeks after the last menstrual period. Suitable preparation methods are described in Shamblott et al., Proc. Natl. Acad. Sci. USA 95:13726,1998 and International Patent Application WO 98/43679.

Briefly, genital ridges are rinsed with isotonic buffer, then placed into 0.1 mL 0.05% trypsin-0.53 mM Sodium EDTA solution (BRL) and cut into <1 mm$^3$ chunks. The tissue is then pipetted through a 100 μL pipet tip to further disaggregate the cells. It is incubated at 37° C. for approximately 5 min, then approximately 3.5 mL EG growth medium is added. EG growth medium is DMEM, 4500 mg/L D-glucose, 2200 mg/L mM sodium bicarbonate; 15% ES qualified fetal calf serum (BRL); 2 mM glutamine (BRL); 1 mM sodium pyruvate (BRL); 1000-2000 U/mL human recombinant leukemia inhibitory factor (LIF, Genzyme); 1-2 ng/ml human recombinant basic fibroblast growth factor (bFGF, Genzyme); and 10 μM forskolin (in 10% DMSO).

Ninety-six well tissue culture plates are prepared in advance with a sub confluent layer of feeder cells cultured for 3 days in a modified EG growth medium free of LIF, bFGF or Forskolin, then irradiated with 5000 rad γ-irradiation. Suitable feeders are STO cells (ATCC Accession No. CRL 1503). ~0.2 mL of the primary germ cell suspension is added to each of the prepared wells. The first passage is conducted after 7-10 days in EG growth medium, transferring each well to 1 well of a 24-well culture dish previously prepared with irradiated STO mouse fibroblasts.

Undifferentiated pPS cells have characteristic morphological features, with high nuclear/cytoplasmic ratios, prominent nucleoli, and compact colony formation with poorly discernable cell junctions. It is desirable to obtain cells that have a "normal karyotype", which means that the cells are euploid, wherein all human chromosomes are present and are not noticeably altered. This characteristic is also desirable in any differentiated cells that are subsequently derived and propagated.

Characteristic embryonic antigens can be identified by immunohistochemistry or flow cytometry, using antibodies for SSEA 1, SSEA-3 and SSEA-4 (Developmental Studies Hybridoma Bank, National Institute of Child Health and Human Development, Bethesda Md.), and TRA-1-60 and TRA-1-81 (Andrews et al., in Robertson E, ed. Teratocarcinomas and Embryonic Stem Cells. IRL Press, 207-246, 1987). The SSEA-1 marker is typically low or absent on hES cells, but present on hEG cells. Differentiation of cells in vitro generally results in the loss of SSEA-3, SSEA-4, TRA-1-60, and TRA-1-81, and increased expression of SSEA-1. pPS cells can also be characterized by the presence of alkaline phosphatase activity, which can be detected by developing fixed cells with Vector Red as a substrate (Vector Laboratories, Burlingame Calif.), and detecting red fluorescence of the product using a rhodamine filter system.

Pluripotency of embryonic stem cells can be confirmed by injecting approximately 0.5-10×10$^6$ cells into the rear leg muscles of 8-12 week old male SCID mice. The resulting tumors can be fixed in 4% paraformaldehyde and examined histologically after paraffin embedding at 8-16 weeks of development. Teratomas develop that demonstrate at least one cell type of each of the three germ layers, such as cartilage, smooth muscle, and striated muscle (for mesoderm); stratified squamous epithelium with hair follicles, neural tube with ventricular, intermediate, and mantle layers (for ectoderm); ciliated columnar epithelium and villi lined by absorptive enterocytes and mucus-secreting goblet cells (for endoderm).

Propagation of pPS Cells

Embryonic stem cells can be cultured on layers of feeder cells in a nutrient medium. The ES cells are routinely split every 1-2 weeks by brief trypsinization, exposure to Dulbecco's PBS (without calcium or magnesium and with 2 mM EDTA), exposure to Dispase or to Type IV Collagenase (1 mg/ml; Gibco) or by selection of individual colonies by micropipette. Clump sizes of about 50 to 100 cells are optimal. Alternatively, after incubation with the protease, cultures can be scraped, dissociated into small clusters, and re-seeded onto fresh feeder cells at a split ratio of 1:3 to 1:30.

Embryonic germ cells can be cultured on feeder cells with daily replacement of growth medium until cells morphology consistent with EG cells are observed, typically, 7-30 days with 1 to 4 passages. The cells maintain their pluripotency through several months of culture.

International Patent Application WO 99/20741 describes methods and materials for growing pluripotent stem cells in the absence of feeder cells, on an extracellular matrix with a nutrient medium. Suitable are fibroblast matrices prepared from lysed fibroblasts or isolated matrix component from a number of sources. The nutrient medium may contain sodium pyruvate, nucleosides, and one or more endogenously added growth factors, such as bFGF, and may be conditioned by culturing with fibroblasts.

In the absence of feeder cells, suitable substrates for propagation of pPS include extracellular matrix components, such as Matrigel® (Becton Dickenson) or laminin. Matrigel® is a soluble preparation of extracellular matrix from Engelbreth-Holm-Swarm tumor cells that gels at room temperature to form a reconstituted basement membrane. To avoid the effect of growth factors present in the membrane (such as IGF-1, TGF, and PDGF), Growth Factor Reduced Matrigel® is available. The critical components of the matrix can be identified by preparing an artificial mixture of all the components and leaving out components seriatim to determine the effect. Other mixtures of extracellular matrix components may also be suitable. Examples include collagen, fibronectin, proteoglycan, entactin, heparan sulfate, and the like, in various combinations.

The pluripotent cells are then plated onto the substrate in a suitable distribution and in the presence of a medium that promotes cell survival, propagation, and retention of the desirable characteristics. All these characteristics benefit from careful attention to the seeding distribution. One feature of the distribution is the plating density. It has been found that plating densities of at least about 15,500 cells $cm^{-2}$ promote survival and limit differentiation. Typically, a plating density of between about 90,000 $cm^{-2}$ and about 170,000 $cm^{-2}$ is used.

Another significant feature is the dispersion of cells. The propagation of mouse stem cells involves dispersing the cells into a single-cell suspension (Robinson, Meth. Mol. Biol. 75:173, 1997 at page 177). In contrast, the passage of pPS cells in the absence of feeders benefits from preparing the pPS cells in small clusters. Typically, enzymatic digestion is halted before cells become completely dispersed (say, ~5 min with collagenase IV). The plate is then scraped gently with a pipette, and the cells are triturated with the pipette until they are suspended as clumps of adherent cells, about 10-2000 cells in size. The clumps are then plated directly onto the substrate without further dispersal.

It has also been found that pPS cells plated in the absence of fresh feeder cells benefit from being cultured in a nutrient medium. The medium will generally contain the usual components to enhance cell survival, including isotonic buffer, essential minerals, and either serum or a serum replacement of some kind. Also beneficial is a medium that has been conditioned to supply some of the elements provided by feeder cells. Conditioned medium can be prepared by culturing irradiated primary mouse embryonic fibroblasts (or another suitable cell preparation) at a density of $5 \times 10^5$ cells per 9.6 $cm^2$ well in a serum replacement medium such as KO DMEM plus 20% serum replacement, containing 4 ng/mL basic fibroblast growth factor (bFGF). The culture supernatant is harvested after 1 day at 37° C., and typically supplemented with additional growth factors that benefit pPS cell culture. For hES, a growth factor like bFGF is often used. For hEG, culture medium may be supplemented with a growth factor like bFGF, an inducer of gp130, such as LIF or Oncostatin-M, and perhaps a factor that elevates cyclic AMP levels, such as forskolin. Various types of pPS cells may benefit from other factors in the medium.

Cell populations propagated by several of these techniques often remain essentially undifferentiated through multiple passages over a number of months. It is recognized that during certain passages, some cells around the periphery of colonies may differentiate (particularly when replated as single cells, or when large clusters are allowed to form). However, cultures typically reestablish a larger proportion of undifferentiated cells with characteristic morphology during the culture period. Optimally, the propagated cells will have a doubling time of no more than about 20-40 hours.

Materials and Procedures for Differentiating pPS Cells

Differentiated cells of this invention can be made by culturing pPS cells in the presence of a hepatocyte differentiation agent. Optionally, the cells are also cultured in the presence of a hepatocyte maturation factor, either simultaneously or sequentially to when they are cultured with the differentiation agent. The resulting cells have phenotypic characteristics of the hepatocyte lineage, as described in the section that follows.

In certain embodiments of the invention, differentiation of the pPS is initiated by first forming embryoid bodies. General principles in culturing embryoid bodies are reported in O'Shea, Anat. Rec. (New Anat.) 257:323, 1999. pPS cells are cultured in a manner that permits aggregates to form, for which many options are available: for example, by overgrowth of a donor pPS cell culture, or by culturing pPS cells in culture vessels having a substrate with low adhesion properties, such as methyl cellulose. Embryoid bodies are readily recognizable by those skilled in the art, and can be readily harvested and transferred to a new culture environment. The embryoid bodies will typically have an endoderm exterior, and mesoderm and ectoderm interior.

As illustrated in the example section below, embryoid bodies can also be made in suspension culture. pPS cells are harvested by brief collagenase digestion, dissociated into clusters, and plated in non-adherent cell culture plates. The aggregates are fed every few days, and then harvested after a suitable period, typically 4-8 days. The aggregates are then plated on a substrate suitable for cells of the hepatocyte lineage. Exemplary are Matrigel® (Becton Dickenson), more fully described earlier, laminin, various types of collagen, and gelatin. Other artificial matrix components, and combinations may be used. Matrix can also be produced by first culturing a matrix-producing cell line (such as a line of fibroblasts, endothelial cells, or mesenchymal stem cells), and then lysing and washing away cell debris in such a way that the matrix remains attached to the surface of the vessel. Dispersion of cells from the embryoid bodies is not usually necessary; the embryoid bodies can be plated directly onto the matrix. The cells are then cultured in a medium that contains the hepatocyte differentiation agent.

In other embodiments of this invention, the pPS cells are combined with the differentiation agent without forming substantial numbers of embryoid bodies—i.e., by adding the agent to a standard pPS cell culture at or before the time it reaches confluence, but before it begins to overgrow. This is referred to in this disclosure as the direct differentiation method. It is generally advantageous (but not required) that the pPS cells are in a feeder-free culture. pPS cells can be harvested and plated onto a new substrate, and medium containing the differentiation agent can be added. Alternatively, if the pPS cells are already being maintained on a matrix suitable for culture of the differentiated cells, then the differentiation agent can be added directly to the pPS culture without replating. The cultures are inspected daily to determine whether confluence is reached. It has been found that the yield of hepatocyte lineage cells can be as much as 3-fold higher when the differentiation agent is added just as the cells reach confluence, rather than at ~60-80% confluence.

Differentiation to the hepatocyte lineage is further promoted by providing a substrate typical of the environment for hepatocytes in vivo. For example, certain extracellular matrix components provide a suitable surface, such as Matrigel® (Becton Dickenson), laminin, or matrix obtained from lysed cells. Another suitable substrate for differentiation of these cells is gelatin. The cells are cultured in a nutrient medium that contains buffer, ionic strength, and nutrients adequate to maintain the cells (see generally WO 99/20741). Optimization of medium for particular cells is within purview of the skilled practitioner, and is exemplified elsewhere in this disclosure.

The cells are maintained in the environment containing a suitable substrate and the hepatocyte differentiation agent for a period of time sufficient to permit enrichment of the differentiated cells from other cells—as may be determined empirically. For example, the first day of culture with a differentiation agent such as n-butyrate leads to release of about 90% of cultured embryoid body derived cells from the substrate into the medium. These cells are then removed when the medium is changed after 24 h, and the surviving cells are cultured in fresh medium containing n-butyrate.

After sufficient culture period, the remaining cells are considerably enriched for those having characteristics of hepatocytes and/or hepatocyte progenitor cells. For the hepatocyte differentiation agent n-butyrate, the culture period is typically about 4-8 days, often about 6 days. The reader is cautioned that prolonged culture in the presence of some of the differentiation agents of this invention may be suboptimal for maximizing yield of hepatocyte lineage cells. Other differentiation agents such as n-butyrate are tolerated on an ongoing basis. Under these circumstances, it can be advantageous to keep the agent in the medium to maintain the full phenotype of the differentiated cell. Without intending to be limited by theory, it is a hypothesis of this invention that hepatocyte differentiation agents such as n-butyrate may have two effects: first, to promote differentiation of pPS cells down the hepatocyte lineage, and second, to preferentially select cells of this lineage for survival as the culture continues.

Suitable Differentiation Agents n-Butyrate is a model hepatocyte differentiation agent, illustrated in the examples that follow. Those skilled in the art will readily recognize that a number of homologs of n-butyrate can readily be identified that have a similar effect, and can be used as substitutes in the practice of this invention.

One class of homologs consists of other hydrocarbons that have similar structural and physicochemical properties to those of n-butyrate. Some of such homologs are acidic hydrocarbons comprising 3-10 carbon atoms in branched, straight-chain or cyclic form, and a conjugate base selected from the group consisting of a carboxylate, a sulfonate, a phosphonate, and other proton donors. Suitable examples include but are not limited to n-butyric acid, isobutyric acid, 2-butenoic acid, 3-butenoic acid, propanoic acid, propenoic acid, pentanoic acid, pentenoic acid, other short-chain fatty acids that are either saturated or unsaturated, amino butyric acid, phenyl butyric acid, phenyl propanoic acid, phenyl acetic acid, phenoxyacetic acid, cinnamic acid, and dimethylbutyrate. Also of interest is a hydrocarbon sulfonate or phosphonate that is isosteric with such compounds, particularly propanesulfonic acid and propanephosphonic acid, which are isosteric to n-butyrate.

In the naming of such compounds, it is understood that all stereoisomers are included unless explicitly stated otherwise. Compounds with acidic groups may be provided in the acidic form or as the conjugate base, with any acceptable opposing counter-ion. Since the use of sodium n-butyrate would increase the ionic strength of the environment it is used in, the action of other agents may be augmented by providing a change in ionic strength, by adding a salt, if necessary.

Another class of homologs are derivatives of butyrate and butyrate homologs, including conjugates with other molecules, such as amino acids, monosaccharides, and other acceptable conjugate pairs. Many such derivatives have been developed as butyrate prodrugs that are transformed to the active form in vivo or in situ by the presence of a suitable converting enzyme—for example, a protease or a glycosidase. By way of illustration, members of this class include arginine butyrate, lysine butyrate, other butyrate amides, glucose pentabutyrate, tributyrin, diacetone glucose butyrate, other butyrate saccharides, aminobutyric acid, isobutyramide, pivaloyloxymethyl butyrate, 1-(2-hydroxyethyl)4-)1-oxobutyl)-piperazine butyrate, other piperazine derivatives of butyrate, and piracetam (2-oxo-1-pyrrolidine acetamide, Notropyl™), a cyclic derivative of gamma-amino butyrate.

A further class of homologs are inhibitors of histone deacetylase. Non-limiting examples include trichostatin A, 5-azacytidine, trapoxin A, oxamflatin, FR901228, cisplatin, and MS-27-275. The reader is also referred to antiprotosoal cyclic tetrapeptides in U.S. Pat. No. 5,922,837; antibacterial agents in U.S. 5,925,659; corepressor inhibitors in WO 99/23885; and cyclic peptide derivatives in WO 99/11659. Methods to identify compounds with histone deacetylase inhibitors can be identified by de-repression of hormone receptor compounds (WO 98/48825).

The hepatocyte differentiation activity of n-butyrate may rely at least in part on an ability to inhibit histone deacetylase. Assays for histone deacetylase activity can be used as a preliminary screen to select candidates for other differentiation agents. Many such assays are available. For example, U.S. Pat. No. 5,922,837 (col. 3 ff.) describes an assay using tritiated N-desmethoxyapicidin and a parasite or chick liver S100 solution as a source of deacetylase activity. The candidate compound is added to the reaction mixture, and tritium release is measured using a filter method. Nare et al. (Anal. Biochem. 267:390, 1999) have developed a scintillation proximity assay using a peptide from histone H4, with lysine ∈-amino groups acetylated with tritium, and bound to an SPA bead that scintillates proportionately to the amount of proximal tritium. Histone deacetylase activity (obtained from extracts of HeLa cell nuclei) releases the labeled acetyl groups and decreases scintillation, and the presence of a deacetylase inhibitor maintains scintillation. Hoffman et al. (Nucl. Acids Res. 27:2057, 1999) describes a non-isotopic assay for histone deacetylase activity. A fluorescent substrate has been developed that is an aminocoumarine derivative of $\Omega$-acetylated lysine. This permits quantitation of substrate in the nanomolar concentration range, which allows for high throughput screening of histone deacetylase inhibitors.

A definitive test for a suitable differentiation agent is its ability to transform pPS cell cultures into cultures enriched for cells of the hepatocyte lineage, as described in this disclosure. Candidate compounds, optionally prescreened according to one or more of the above-listed criteria, are added to cultures of pPS cells or embryoid bodies in a manner similar to what is known to be effective for n-butyrate. Any compound that can at least promote differentiation of pPS cells down the hepatocyte lineage, or preferentially permit the growth of hepatoblast-type cells, or preferentially remove cells of other lineages, will be beneficial in deriving certain differentiated cell populations embodied in this invention.

Following these guidelines, the ability of particular compound or combination of compounds to act as hepatocyte differentiation agents comprises culturing a population of substantially undifferentiated pPS cells, or a mixed population of differentiated pPS cells (such as those obtained from embryoid bodies or by overgrowth of a pPS culture) in the presence of the compound, and then determining the effect on cell morphology, marker expression, enzymatic activity, proliferative capacity, or other features of interest in relation to cells of the hepatocyte lineage. For optimum results, several concentrations of the test compound are evaluated. A suitable base concentration may be isoosmolar or isotonic with effective butyrate concentrations, or have equivalent inhibitory capacity of another histone deacetylase. The compound can then be tested over a range of about $1/10^{th}$ to 10 times the base concentration, or more, to determine if it has the desired hepatocyte differentiation capacity.

A compound will be considered effective as a differentiation agent if it is capable of producing from a culture of pPS cells or embryoid body cells a population of cells in which at least 40% of the cells have at least three characteristics of hepatoblasts or hepatocytes. Agents that produce more uniform populations having a greater number of hepatocyte characteristics are advantageous in some contexts. It is recognized that agents producing less uniform or less mature hepatocyte populations may also be advantageous if the cells retain another desirable feature (such as hardiness to manipulation, or proliferation capacity). As described below, such cell populations can be further enriched for the desired cell type by sorting or adsorption techniques.

Optional Use of Maturation Factors

Enrichment for differentiated cells using a hepatocyte differentiation agent can be supplemented, if desired, by the use of a separate compound or mixture of compounds that act as hepatocyte maturation factors. Such agents may augment the phenotype change promoted by the differentiation agent, or they may push the differentiation pathway further towards more mature cells, or they may help select for cells of the hepatocyte lineage (for example, by preferentially supporting their survival), or they may promote more rapid proliferation of cells with the desired phenotype.

Once class of hepatocyte maturation factors are soluble growth factors (peptide hormones, cytokines, ligand-receptor complexes, and the like) that are capable of promoting the growth of cells of the hepatocyte lineage. Such factors include but are not limited to epidermal growth factor (EGF), insulin, TGF-α, TGF-β, fibroblast growth factor (FGF), heparin, hepatocyte growth factor (HGF), Oncostatin M in the presence of dexamethazone, IL-1, IL-6, IGF-I, IGF-II, HBGF-1, and glucagon.

Another class of hepatocyte maturation factors are corticosteroids, particularly glucocorticoids. Such compounds are a steroid or steroid mimetic, and affects intermediary metabolism, especially promotion of hepatic glycogen deposition, and inhibiting inflammation. Included are naturally occurring hormones exemplified by cortisol, and synthetic glucocorticoids such as dexamethazone (U.S. Pat. No. 3,007,923) and its derivatives, prednisone, methylprednisone, hydrocortisone, and triamcinolone (U.S. Pat. No. 2,789,118) and its derivatives.

Another class of hepatocyte maturation factors are organic solvents like DMSO. Alternatives with similar properties include but are not limited to dimethylacetamide (DMA), hexmethylene bisacetamide, and other polymethylene bisacetamides. Solvents in this class are related, in part, by the property of increasing membrane permeability of cells. Also of interest are solutes such as nicotinamide. Testing for whether a candidate compound acts as a hepatocyte maturation factor for the purpose of this invention is performed empirically: pPS cultures are differentiated into cells of the hepatocyte lineage using a hepatocyte differentiation agent described above, in combination with a model hepatocyte differentiation agent, such as a growth factor or DMSO (the positive control). In parallel, pPS are subjected to a similar protocol using the same differentiation agent and the candidate maturation factor. Resultant cells are then compared phenotypically to determine whether the candidate agent has a similar effect to that of the positive control.

In particular embodiments of this invention, the hepatocyte differentiation agent and the hepatocyte maturation factor are used simultaneously or sequentially. In one illustration, newly plated embryoid bodies or feeder-free pPS cultures are placed in a medium containing both n-butyrate and DMSO, and cultured for 4, 6, or 8 days, or until characteristic features appear, replacing the medium periodically (say, every 24 h) with fresh medium containing n-butyrate and DMSO. In another illustration, EB or pPS cultures are first cultured with n-butyrate and DMSO for 4, 6, or 8 days, then the medium is exchanged for a hepatocyte-friendly medium containing a cocktail of growth factors (perhaps in combination with n-butyrate) for long-term culture or assay.

Following these guidelines, the ability of particular compound or combination of compounds to act as hepatocyte maturation factors comprises culturing a population of cells previously treated with a hepatocyte differentiation agent in the presence of the compound, or including the compound in a culture of cells being treated with a hepatocyte differentiation factor. The effect of the compound on cell morphology, marker expression, enzymatic activity, proliferative capacity, or other features of interest is then determined in comparison with parallel cultures that did not include the candidate compound. For optimum results, several concentrations of the test compound are evaluated. A suitable base concentration for organic solvents may be isoosmolar or isotonic with effective DMSO concentrations. Suitable base concentrations for growth factors, cytokines, and other hormones may be concentrations known to have similar growth-inducing or hormone activity in other systems. The test compound can then be tested over a range of about $\frac{1}{10}^{th}$ to 10 times the base concentration to determine if it has the desired effect on hepatocyte-directed maturation of pPS cells.

Once cells of the desired phenotype are obtained, the cells can be harvested for any desired use. In certain differentiated cell populations of this invention, the cells are sufficiently uniform in phenotype that they can be harvested simply by releasing the cells from the substrate (e.g., using collagenase or by physical manipulation), and optionally washing the cells free of debris. If desired, the harvested cells can be further processed by positive selection for desired features, or negative selection for undesired features. For example, cells expressing surface markers or receptors can be positively or negatively selected by incubating the population with an antibody or conjugate ligand, and then separating out the bound cells—for example, by labeled sorting techniques, or adsorption to a solid surface. Negative selection can also be performed by incubating the population with a cytolytic antibody specific for the undesired marker, in the presence of complement.

If desired, harvested cells can be transferred into other culture environments, such as those described elsewhere for the propagation of other types of hepatocyte preparations. See, for example, U.S. Pat. Nos. 5,030,105 and 5,576,207; EP Patent Application EP 953,633; Angelli et al., Histochem. J. 29:205, 1997; Gomez-Lechon et al., p. 130 ff. in In vivo Methods in Pharmaceutical Research, Academic Press, 1997).

Characteristics of Differentiated Cells

Cells can be characterized according to a number of phenotypic criteria. The criteria include but are not limited to the detection or quantitation of expressed cell markers, and enzymatic activity, and the characterization of morphological features and intercellular signaling.

Certain differentiated pPS cells embodied in this invention have morphological features characteristic of hepatocytes. The features are readily appreciated by those skilled in evaluating such things, and include any or all of the following: a polygonal cell shape, a binucleate phenotype, the presence of rough endoplasmic reticulum for synthesis of secreted protein, the presence of Golgi-endoplasmic reticulum lysosome complex for intracellular protein sorting, the presence of peroxisomes and glycogen granules, relatively abundant mitochondria, and the ability to form tight intercellular junctions resulting in creation of bile canalicular spaces. A number of these features present in a single cell is consistent with the cell being a member of the hepatocyte lineage. Unbiased determination of whether cells have morphologic features characteristic of hepatocytes can be made by coding micrographs of differentiated pPS cells, adult or fetal hepatocytes, and one or more negative control cells, such as a fibroblast, or RPE (Retinal pigment epithelial) cells—then evaluating the micrographs in a blinded fashion, and breaking the code to determine if the differentiated pPS cells are accurately identified.

Cells of this invention can also be characterized according to whether they express phenotypic markers characteristic of cells of the hepatocyte lineage. Cell markers useful in distinguishing liver progenitors, hepatocytes, and biliary epithelium, are shown in Table 1 (adapted from p 35 of Sell & Zoran, Liver Stem Cells, R. G. Landes Co., Texas, 1997; and Grisham et al., p 242 of "Stem Cells", Academic Press, 1997).

TABLE 1

Liver Cell Markers

|  | early progenitors | hepato-cytes | biliary epithelium |  | early progenitors | hepato-cytes | biliary epithelium |
|---|---|---|---|---|---|---|---|
| albumin | + | + | − | OC.1 | − | − | + |
| $\alpha_1$-antitrypsin | + | + | − | OC.2 | + | − | + |
| α-fetoprotein | + | fetal & postnatal | − | OC.3 | + | − | + |
| CEA | − | − | + (?) | BD.1 | + | − | + |
| γ-glutamyl tranpeptidase | + | fetal | + | A6 | + | − | + |
| GST-P | + | fetal | + | HBD.1 | + | + | + |
| glucose-6-phosphatase | + | + | − | H.2 | − | + | − |
| catalase | − | + | − | H.4 | − | + | − |
| M2-PK | + | fetal | + | H-4 | ? | + | − |
| L-PK | − | + | fetal | H-6 | − | + | − |
| p450 mono-oxygenase | + | + | − | $HES_6$ | − | + | − |
| p-glycoprotein | ? | canaliculi | − | RL16/79 | − | postnatal | − |
| CK7 | − | − | + | RL23/36 | − | + | − |
| CK8 | + | + | + | $BPC_5$ | + | − | − |
| CK14 | + | − | − | Vimentin | − | − | fetal |
| CK18 | + | + | + | HepPar1 | + | + | − |
| CK19 | − (+) | − | + | Cell-CAM 105 | + | + | − |
| CKX | + | − | + | DPP IV | + | canaliculi | + |
| $BDS_7$ | + | − | + | lectin binding sites | + | − | + |

TABLE 1-continued

Liver Cell Markers

|  | early progenitors | hepatocytes | biliary epithelium |  | early progenitors | hepatocytes | biliary epithelium |
|---|---|---|---|---|---|---|---|
| OV1 | + | − | + | blood group antigens | + | − | + |
| OV6 | − | − | + | | | | |

It has been reported that hepatocyte differentiation requires the transcription factor HNF-4α (Li et al., Genes Dev. 14:464, 2000). Markers independent of HNF-4α expression include α1-antitrypsin, α-fetoprotein, apoE, glucokinase, insulin growth factors 1 and 2, IGF-1 receptor, insulin receptor, and leptin. Markers dependent on HNF-4α expression include albumin, apoAI, apoAII, apoB, apoCIII, apoCII, aldolase B, phenylalanine hydroxylase, L-type fatty acid binding protein, transferrin, retinol binding protein, and erythropoietin (EPO). Other markers of interest include those exemplified in Examples 1, 2, and 6, below.

Assessment of the level of expression of such markers can be determined in comparison with other cells. Positive controls for the markers of mature hepatocytes include adult hepatocytes of the species of interest, and established hepatocyte cell lines, such as the HepG2 line derived from a hepatoblastoma reported in U.S. Pat. No. 5,290,684. The reader is cautioned that permanent cell lines such as HepG2 may be metabolically altered, and fail to express certain characteristics of primary hepatocytes such as cytochrome p450. Cultures of primary hepatocytes may also show decreased expression of some markers after prolonged culture. Negative controls include cells of a separate lineage, such as an adult fibroblast cell line, or retinal pigment epithelial (RPE) cells. Undifferentiated pPS cells are positive for some of the markers listed above, but negative for markers of mature hepatocytes, as illustrated in the examples below.

Tissue-specific protein and oligosaccharide determinants listed in this disclosure can be detected using any suitable immunological technique—such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. Expression of an antigen by a cell is said to be "antibody-detectable" if a significantly detectable amount of antibody will bind to the antigen in a standard immunocytochemistry or flow cytometry assay, optionally after fixation of the cells, and optionally using a labeled secondary antibody or other conjugate (such as a biotin-avidin conjugate) to amplify labeling.

The expression of tissue-specific markers can also be detected at the mRNA level by Northern blot analysis, dot-blot hybridization analysis, or by reverse transcriptase initiated polymerase chain reaction (RT-PCR) using sequence-specific primers in standard amplification methods. See U.S. Pat. No. 5,843,780 for further details. Sequence data for the particular markers listed in this disclosure can be obtained from public databases such as GenBank (URL www.ncbi.nlm.nih.gov:80/entrez). Expression at the mRNA level is said to be "detectable" according to one of the assays described in this disclosure if the performance of the assay on cell samples according to standard procedures in a typical controlled experiment results in clearly discernable hybridization or amplification product. Expression of tissue-specific markers as detected at the protein or mRNA level is considered positive if the level is at least 2-fold, and preferably more than 10- or 50-fold above that of a control cell, such as an undifferentiated pPS cell, a fibroblast, or other unrelated cell type.

Cells can also be characterized according to whether they display enzymatic activity that is characteristic of cells of the hepatocyte lineage. For example, assays for glucose-6-phosphatase activity are described by Bublitz (Mol Cell Biochem. 108:141, 1991); Yasmineh et al. (Clin. Biochem. 25:109, 1992); and Ockerman (Clin. Chim. Acta 17:201, 1968). Assays for alkaline phosphatase (ALP) and 5-nucleotidase (5'-Nase) in liver cells are described by Shiojiri (J. Embryol. Exp. Morph.62:139, 1981). A number of laboratories that serve the research and health care sectors provide assays for liver enzymes as a commercial service.

Cytochrome p450 is a key catalytic component of the mono-oxygenase system. It constitutes a family of hemoproteins responsible for the oxidative metabolism of xenobiotics (administered drugs), and many endogenous compounds. Different cytochromes present characteristic and overlapping substrate specificity. Most of the biotransforming ability is attributable by the cytochromes designated 1A2, 2A6, 2B6, 3A4, 2C9-11, 2D6, and 2E1 (Gomes-Lechon et al., pp 129-153 in "In vitro Methods in Pharmaceutical Research," Academic Press, 1997).

A number of assays are known in the art for measuring cytochrome p450 enzyme activity. For example, cells can be contacted with a non-fluorescent substrate that is convertible to a fluorescent product by p450 activity, and then analyzed by fluorescence-activated cell counting (U.S. Pat. No. 5,869,243). Specifically, the cells are washed, and then incubated with a solution of 10 μM/L 5,6-methoxycarbonylfluorescein (Molecular Probes, Eugene Oreg.) for 15 min at 37° C. in the dark. The cells are then washed, trypsinized from the culture plate, and analyzed for fluorescence emission at ~520-560 nm. A cell is said to have the enzyme activity assayed for if the level of activity in a test cell is more than 2-fold, and preferably more than 10- or 100-fold above that of a control cell, such as a fibroblast.

The expression of cytochrome p450 can also be measured at the protein level, for example, using specific antibody in Western blots, or at the mRNA level, using specific probes and primers in Northern blots or RT-PCR. See Borlakoglu et al., Int. J. Biochem. 25:1659, 1993. Particular activities of the p450 system can also be measured: 7-ethoxycoumarin O-de-ethylase activity, aloxyresorufin O-de-alkylase activity, coumarin 7-hydroxylase activity, p-nitrophenol hydroxylase activity, testosterone hydroxylation, UDP-glucuronyltransferase activity, glutathione S-transferase activity, and others (reviewed in Gomes-Lechon et al., pp 411-431 in "In vitro Methods in Pharmaceutical Research,"

Academic Press, 1997). The activity level can then be compared with the level in primary hepatocytes, as shown in Table 2.

TABLE 2

Drug Metabolizing Activities in 24-H Primary Cultured Human Hepatocytes

| Isozyme | Reaction | Activity | |
|---|---|---|---|
| Phase I | | | |
| P450† | | 65 ± 8 | (n = 10) |
| NADPH-Cc‡ | Cytochrome c oxidation | 23 ± 2 | (n = 10) |
| CYP1A1/2d§ | Aryl hydrocarbon hydroxylation | 2.93 ± 0.99 | (n = 7) |
| | 7-Ethoxyresorufin O-de-ethylation | 3.09 ± 2.52 | (n = 14) |
| CYP2A6§ | Coumarin 7-hydroxylation | 137 ± 42 | (n = 6) |
| CYP2B6§ | 7-Pentoxyresorufin O-depentylation | 3.28 ± 1.76 | (n = 10) |
| | 7-Benzoxyresorufin O-debenzylation | 1.38 ± 0.33 | (n = 5) |
| CYP2C9§ | 4'-Diclofenac hydroxylation | 317 ± 73 | (n = 9) |
| CYP2E1§ | p-Nitrophenol hydroxylation | 89 ± 42 | (n = 6) |
| | Chlorzoxazone 6-hydroxylation | 27 ± 3 | (n = 3) |
| CYP3A3-5§ | Testosterone 6β-hydroxylation | 195 ± 122 | (n = 7) |
| | Testosterone 2β-hydroxylation | 61 ± 16 | (n = 7) |
| | Testosterone 15β-hydroxylation | 12.4 ± 8.6 | (n = 7) |
| Phase II | | | |
| mEH§ | Benzo(a)pyrene 7, 8-oxide hydration | 180 ± 72 | (n = 10) |
| UDPG-t‡ | 4-Methylumbelliferone conjugation | 3.6 ± 0.4 | (n = 5) |
| GSH-t‡ | 1-Chloro-2,4-dinitrobenzene conjugation | 301 ± 112 | (n = 8) |

*Mean ± s.d. enzymatic activity determined in 24-h cultured human hepatocytes.
†Cytochrome P450 content is expressed as picomoles per milligram of cellular protein.
‡NADPH-C, UDPG-t and GSH-t activities are expressed as nanomoles per milligram per minute.
§CYP enzymatic activities are expressed as picomoles per milligram per minute.

Assays are also available for enzymes involved in the conjugation, metabolism, or detoxification of small molecule drugs. For example, cells can be characterized by an ability to conjugate bilirubin, bile acids, and small molecule drugs, for excretion through the urinary or biliary tract. Cells are contacted with a suitable substrate, incubated for a suitable period, and then the medium is analyzed (by GCMS or other suitable technique) to determine whether conjugation product has been formed. Drug metabolizing enzyme activities include de-ethylation, dealkylation, hydroxylation, demethylation, oxidation, glucuroconjugation, sulfoconjugation, glutathione conjugation, and N-acetyl transferase activity (A. Guillouzo, pp 411-431 in "In vitro Methods in Pharmaceutical Research," Academic Press, 1997). Assays include peenacetin de-ethylation, procainamide N-acetylation, paracetamol sulfoconjugation, and paracetamol glucuronidation (Chesne et al., pp 343-350 in "Liver Cells and Drugs", A. Guillouzo ed. John Libbey Eurotext, London, 1988).

Cells of the hepatocyte lineage can also be evaluated on their ability to store glycogen. A suitable assay uses Periodic Acid Schiff (PAS) stain, which does not react with mono- and disaccharides, but stains long-chain polymers such as glycogen and dextran. PAS reaction provides quantitative estimations of complex carbohydrates as well as soluble and membrane-bound carbohydrate compounds. Kirkeby et al. (Biochem. Biophys. Meth. 24:225, 1992) describe a quantitative PAS assay of carbohydrate compounds and determgents. van der Laarse et al. (Biotech Histochem. 67:303, 1992) describe a microdensitometric histochemical assay for glycogen using the PAS reaction. Evidence of glycogen storage is determined if the cells are PAS-positive at a level that is at least 2-fold, and preferably more than 10-fold above that of a control cell, such as a fibroblast. The cells can also be characterized by karyotyping according to standard methods.

pPS cells differentiated according to this invention can have a number of the aforementioned features, including antibody-detectable expression of $\alpha_1$-antitrypsin (AAT) or albumin; absence of antibody-detectable expression of $\alpha$-fetoprotein; RT-PCR detectable expression of asialoglycoprotein receptor (either the ASGR-1 or ASGR-2 isotype); evidence of glycogen storage; evidence of cytochrome p450 or glucose-6-phosphatase activity; and morphological features characteristic of hepatocytes. The more of these features that are present in a particular cell, the more it can be characterized as a cell of the hepatocyte lineage. Cells having at least 2, 3, 5, 7, or 9 of these features are increasingly more preferred. In reference to a particular cell population as may be present in a culture vessel or a preparation for administration, uniformity between cells in the expression of these features is often advantageous. In this circumstance, populations in which at least about 40%, 60%, 80%, 90%, 95%, or 98% of the cells have the desired features are increasingly more preferred.

Other desirable features of differentiated cells of this invention are an ability to act as target cells in drug screening assays, and an ability to reconstitute liver function, both in vivo, and as part of an extracorporeal device. These features are further described in sections that follow.

Telomerization of Differentiated Cells

It is desirable that cells of the hepatocyte lineage have the ability to replicate in certain drug screening and therapeutic applications. The cells of this invention can optionally be telomerized to increase their replication potential, either before or after they progress to restricted developmental lineage cells or terminally differentiated cells. pPS cells that are telomerized may be taken down the differentiation pathway described earlier; or differentiated cells can be telomerized directly.

Before and after telomerization, telomerase activity and expression of hTERT gene product can be determined using reagents and methods known in the art. For example, pPS cells are evaluated for telomerase using TRAP activity assay (Kim et al., Science 266:2011, 1997; Weinrich et al., Nature Genetics 17:498, 1997). Expression of hTERT at the mRNA level is evaluated by RT-PCR.

Cells are telomerized by genetically altering them by transfection or transduction with a suitable vector, homologous recombination, or other appropriate technique, so that they express the telomerase catalytic component (TERT). Particularly suitable is the catalytic component of human telomerase (hTERT), provided in International Patent Application WO 98/14592. For certain applications, species homologs like mouse TERT (WO 99/27113) can also be used. Transfection and expression of telomerase in human cells is described in Bodnar et al., Science 279:349, 1998 and Jiang et al., Nat. Genet. 21:111, 1999. In another example, hTERT clones (WO 98/14592) are used as a source of hTERT encoding sequence, and spliced into an EcoRI site of a PBBS212 vector under control of the MPSV promoter, or into the EcoRI site of commercially available pBABE retrovirus vector, under control of the LTR promoter. Differentiated or undifferentiated pPS cells are genetically altered using vector containing supernatants over a 8-16 h period, and then exchanged into growth medium for 1-2 days. Genetically altered cells are selected using 0.5-2.5 μg/mL puromycin, and recultured. They can then be assessed for hTERT expression by RT-PCR, telomerase activity (TRAP assay), immunocytochemical staining for hTERT, or replicative capacity. Continuously replicating colonies will be enriched by further culturing under conditions that support proliferation, and cells with desirable phenotypes can optionally be cloned by limiting dilution.

In certain embodiments of this invention, pPS cells are differentiated into cells bearing characteristics of the hepatocyte lineage, and then the differentiated cells are genetically altered to express TERT. In other embodiments of this invention, pPS cells are genetically altered to express TERT, and then differentiated into cells bearing characteristics of the hepatocyte lineage. Successful modification to increase TERT expression can be determined by TRAP assay, or by determining whether the replicative capacity of the cells has improved.

Other methods of immortalizing cells are also contemplated, such as transforming the cells with DNA encoding the SV40 large T antigen (U.S. Pat. No. 5,869,243, International Patent Application WO 97/32972). Transfection with oncogenes or oncovirus products is less suitable when the cells are to be used for therapeutic purposes. Telomerized cells are of particular interest in applications of this invention where it is advantageous to have cells that can proliferate and maintain their karyotype—for example, in pharmaceutical screening, and in therapeutic protocols where differentiated cells are administered to an individual in order to augment liver function.

Use of Differentiated Cells

This invention provides a method by which large numbers of cells of the hepatocyte lineage can be produced. These cell populations can be used for a number of important research, development, and commercial purposes.

Preparation of Expression Libraries and Specific Antibody

The differentiated cells of this invention can also be used to prepare a cDNA library relatively uncontaminated with cDNA preferentially expressed in cells from other lineages. For example, the cells are collected by centrifugation at 1000 rpm for 5 min, and then mRNA is prepared from the pellet by standard techniques (Sambrook et al., supra). After reverse transcribing into cDNA, the preparation can be subtracted with cDNA from any or all of the following cell types: undifferentiated pPS, embryonic fibroblasts, visceral endoderm, sinusoidal endothelial cells, bile duct epithelium, or other cells of undesired specificity, thereby producing a select cDNA library, reflecting expression patterns that are representative of mature hepatocytes, hepatocyte precursors, or both.

The differentiated cells of this invention can also be used to prepare antibodies that are specific for hepatocyte markers, progenitor cell markers, markers that are specific for hepatocyte precursors, and other antigens that may be expressed on the cells. The cells of this invention provide an improved way of raising such antibodies because they are relatively enriched for particular cell types compared with pPS cell cultures and hepatocyte cultures made from liver tissue. Polyclonal antibodies can be prepared by injecting a vertebrate with cells of this invention in an immunogenic form. Production of monoclonal antibodies is described in such standard references as Harrow & Lane (1988), U.S. Pat. Nos. 4,491,632, 4,472,500 and 4,444,887, and *Methods in Enzymology* 73B:3 (1981). Other methods of obtaining specific antibody molecules (optimally in the form of single-chain variable regions) involve contacting a library of immunocompetent cells or viral particles with the target antigen, and growing out positively selected clones. See Marks et al., *New Eng. J. Med.* 335:730, 1996, International Patent Applications WO 94/13804, WO 92/01047, WO 90/02809, and McGuiness et al., *Nature Biotechnol.* 14:1449, 1996. By positively selecting using pPS of this invention, and negatively selecting using cells bearing more broadly distributed antigens (such as differentiated embryonic cells) or adult-derived stem cells, the desired specificity can be obtained. The antibodies in turn can be used to identify or rescue hepatocyte precursor cells of a desired phenotype from a mixed cell population, for purposes such as costaining during immunodiagnosis using tissue samples, and isolating such cells from mature hepatocytes or cells of other lineages.

Genomics

Differentiated pPS cells are of interest to identify expression patterns of transcripts and newly synthesized proteins that are characteristic for hepatocyte precursor cells, and may assist in directing the differentiation pathway or facilitating interaction between cells. Expression patterns of the differentiated cells are obtained and compared with control cell lines, such as undifferentiated pPS cells, other types of committed precursor cells (such as pPS cells differentiated towards other lineages, hematopoietic stem cells, precursor cells for other mesoderm-derived tissue, precursor cells for endothelium or bile duct epithelium, hepatocyte stem cells obtained from adult tissues, or pPS cells differentiated towards the hepatocyte lineage using alternative reagents or techniques).

Suitable methods for comparing expression at the protein level include the immunoassay or immunohistochemistry techniques describe earlier. Suitable methods for comparing expression at the level of transcription include methods of differential display of mRNA (Liang, Peng, et al., Cancer Res. 52:6966, 1992), and matrix array expression systems (Schena et al., Science 270:467, 1995; Eisen et al., Methods Enzymol. 303:179, 1999; Brown et al., Nat. Genet. 21 Suppl 1:33, 1999).

The use of microarray in analyzing gene expression is reviewed by Fritz et al Science 288:316, 2000; "Microarray Biochip Technology", M. Schena ed., Eaton Publishing Company; "Microarray analysis", Gwynne & Page, Science (Aug. 6, 1999 supplement); Pollack et al., Nat Genet 23:41, 1999; Gerhold et al., Trends Biochem. Sci. 24:168, 1999; "Gene Chips (DNA Microarrays)", L Shi, www.Gene-Chips.com. Systems and reagents for performing microarray analysis are available commercially from companies such as Affymetrix, Inc., Santa Clara Calif.; Gene Logic Inc., Columbia Md.; Hyseq Inc., Sunnyvale Calif.; Molecular Dynamics Inc., Sunnyvale Calif.; Nanogen, San Diego Calif.; and Synteni Inc., Fremont Calif. (acquired by Incyte Genomics, Palo Alto Calif.).

Solid-phase arrays are manufactured by attaching the probe at specific sites either by synthesizing the probe at the desired position, or by presynthesizing the probe fragment and then attaching it to the solid support. A variety of solid supports can be used, including glasses, plastics, ceramics, metals, gels, membranes, paper, and beads of various composition. U.S. Pat. No. 5,445,934 discloses a method of on-chip synthesis, in which a glass slide is derivatized with a chemical species containing a photo-cleavable protecting group. Each site is sequentially deprotected by irradiation through a mask, and then reacted with a DNA monomer containing a photoprotective group. Methods for attaching a presynthesized probe onto a solid support include adsorption, ultra violet linking, and covalent attachment. In one example, the solid support is modified to carry an active group, such as hydroxyl, carboxyl, amine, aldehyde, hydrazine, epoxide, bromoacetyl, maleimide, or thiol groups through which the probe is attached (U.S. Pat. Nos. 5,474,895 and 5,514,785).

The probing assay is typically conducted by contacting the array by a fluid potentially containing the nucleotide sequences of interest under suitable conditions for hybridization, and then determining any hybrid formed. For example, mRNA or DNA in the sample is amplified in the presence of nucleotides attached to a suitable label, such as the fluorescent labels Cy3 or Cy5. Conditions are adjusted so that hybridization occurs with precise complementary matches or with various degrees of homology, as appropriate. The array is then washed, and bound nucleic acid is determined by measuring the presence or amount of label associated with the solid phase. Different samples can be compared between arrays for relative levels of expression, optionally standardized using genes expressed in most cells of interest, such as a ribosomal or house-keeping gene, or as a proportion of total polynucleotide in the sample. Alternatively, samples from two or more different sources can be tested simultaneously on the same array, by preparing the amplified polynucleotide from each source with a different label.

An exemplary method is conducted using a Genetic Microsystems array generator, and an Axon GenePix™ Scanner. Microarrays are prepared by first amplifying cDNA fragments encoding marker sequences to be analyzed in a 96 or 384 well format. The cDNA is then spotted directly onto glass slides at a density as high as >5,000 per slide. To compare mRNA preparations from two cells of interest, one preparation is converted into Cy3-labeled cDNA, while the other is converted into Cy5-labeled cDNA. The two cDNA preparations are hybridized simultaneously to the microarray slide, and then washed to eliminate non-specific binding. Any given spot on the array will bind each of the cDNA products in proportion to abundance of the transcript in the two original mRNA preparations. The slide is then scanned at wavelengths appropriate for each of the labels, the resulting fluorescence is quantified, and the results are formatted to give an indication of the relative abundance of mRNA for each marker on the array.

Identifying expression products for use in characterizing and affecting differentiated cells of this invention involves analyzing the expression level of RNA, protein, or other gene product in a first cell type, such as a pPS cell differentiated along the hepatocyte lineage, analyzing the expression level of the same product in a control cell type, comparing the relative expression level between the two cell types, (typically normalized by total protein or RNA in the sample, or in comparison with another gene product expected to be expressed at a similar level in both cell types, such as a house-keeping gene), and identifying products of interest based on the comparative expression level.

Products will typically be of interest if their relative expression level is at least about 2-fold, 10-fold, or 100-fold elevated (or suppressed) in differentiated pPS cells of this invention, in comparison with the control. This analysis can optionally be computer-assisted, by marking the expression level in each cell type on an independent axis, wherein the position of the mark relative to each axis is in accordance with the expression level in the respective cell, and then selecting a product of interest based on the position of the mark. Alternatively, the difference in expression between the first cell and the control cell can be represented on a color spectrum (for example, where yellow represents equivalent expression levels, red indicates augmented expression and blue represents suppressed expression). The product of interest can then be selected based on the color representing expression of one marker of interest, or based on a pattern of colors representing a plurality of markers.

Differentiated pPS Cells for Drug Screening

Differentiated pPS cells of this invention can be used to screen for factors (such as solvents, small molecule drugs, peptides, polynucleotides, and the like) or environmental conditions (such as culture conditions or manipulation) that affect the characteristics of differentiated cells of the hepatocyte lineage.

In some applications, pPS cells (differentiated or undifferentiated) are used to screen factors that promote maturation of cells along the hepatocyte lineage, or promote proliferation and maintenance of such cells in long-term culture. For example, candidate hepatocyte maturation factors or growth factors are tested by adding them to pPS cells in different wells, and then determining any phenotypic change that results, according to desirable criteria for further culture and use of the cells.

Particular screening applications of this invention relate to the testing of pharmaceutical compounds in drug research. The reader is referred generally to the standard textbook "in vitro Methods in Pharmaceutical Research", Academic Press, 1997, and U.S. Pat. No. 5,030,015). In this invention, pPS cells that have differentiated to the hepatocyte lineage play the role of test cells for standard drug screening and toxicity assays, as have been previously performed on hepatocyte cell lines or primary hepatocytes in short-term culture. Assessment of the activity of candidate pharmaceutical compounds generally involves combining the differentiated cells of this invention with the candidate compound, determining any change in the morphology, marker phenotype, or metabolic activity of the cells that is attributable to the compound (compared with untreated cells or cells treated with an inert compound), and then correlating the effect of the compound with the observed change. The screening may be done either because the compound is designed to have a pharmacological effect on liver cells, or because a compound designed to have effects elsewhere may have unintended hepatic side effects. Two or more drugs can be tested in combination (by combining with the cells either simultaneously or sequentially), to detect possible drug-drug interaction effects.

In some applications, compounds are screened initially for potential hepatotoxicity (Castell et al., pp 375-410 in "In vitro Methods in Pharmaceutical Research," Academic Press, 1997). Cytotoxicity can be determined in the first instance by the effect on cell viability, survival, morphology, and leakage of enzymes into the culture medium. More detailed analysis is conducted to determine whether compounds affect cell function (such as gluconeogenesis, ureogenesis, and plasma protein synthesis) without causing toxicity. Lactate dehydrogenase (LDH) is a good marker because the hepatic isoenzyme (type V) is stable in culture conditions, allowing reproducible measurements in culture supernatants after 12-24 h incubation. Leakage of enzymes such as mitochondrial glutamate oxaloacetate transaminase and glutamate pyruvate transaminase can also be used. Gomez-Lechon et al. (Anal. Biochem. 236:296, 1996) describe a microassay for measuring glycogen, which can be applied to measure the effect of pharmaceutical compounds on hepatocyte gluconeogenesis.

Other current methods to evaluate hepatotoxicity include determination of the synthesis and secretion of albumin, cholesterol, and lipoproteins; transport of conjugated bile acids and bilirubin; ureagenesis; cytochrome p450 levels and activities; glutathione levels; release of α-glutathione s-transferase; ATP, ADP, and AMP metabolism; intracellular $K^+$ and $Ca^{2+}$ concentrations; the release of nuclear matrix proteins or oligonucleosomes; and induction of apoptosis (indicated by cell rounding, condensation of chromatin, and nuclear fragmentation). DNA synthesis can be measured as [$^3$H]-thymidine or BrdU incorporation. Effects of a drug on DNA synthesis or structure can be determined by measuring DNA synthesis or repair. [$^3$H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (pp 375-410 in "In vitro Methods in Pharmaceutical Research," Academic Press, 1997) for further elaboration.

Restoration of Liver Function

This invention also provides for the use of differentiated pPS cells to restore a degree of liver function to a subject needing such therapy, perhaps due to an acute, chronic, or inherited impairment of liver function.

To determine the suitability of differentiated pPS cells for therapeutic applications, the cells can first be tested in a suitable animal model. At one level, cells are assessed for their ability to survive and maintain their phenotype in vivo. Differentiated pPS cells are administered to immunodeficient animals (such as SCID mice, or animals rendered immunodeficient chemically or by irradiation) at a site amenable for further observation, such as under the kidney capsule, into the spleen, or into a liver lobule. Tissues are harvested after a period of a few days to several weeks or more, and assessed as to whether pPS cells are still present. This can be performed by providing the administered cells with a detectable label (such as green fluorescent protein, or β-galactosidase); or by measuring a constitutive marker specific for the administered cells. Where differentiated pPS cells are being tested in a rodent model, the presence and phenotype of the administered cells can be assessed by immunohistochemistry or ELISA using human-specific antibody, or by RT-PCR analysis using primers and hybridization conditions that cause amplification to be specific for human polynucleotide sequences. Suitable markers for assessing gene expression at the mRNA or protein level are provided in Table 3. General descriptions for determining the fate of hepatocyte-like cells in animal models is provided in Grompe et al. (Sem. Liver Dis. 19:7, 1999); Peeters et al., (Hepatology 25:884, 1997;) and Ohashi et al. (Nature Med. 6:327, 2000).

At another level, differentiated pPS cells are assessed for their ability to restore liver function in an animal lacking full liver function. Braun et al. (Nature Med. 6:320, 2000) outline a model for toxin-induced liver disease in mice transgenic for the HSV tk gene. Rhim et al. (Proc. Natl. Acad. Sci. USA 92:4942, 1995) and Lieber et al. (Proc. Natl. Acad. Sci. USA 92:6210, 1995) outline models for liver disease by expression of urokinase. Mignon et al. (Nature Med. 4:1185, 1998) outline liver disease induced by antibody to the cell-surface marker Fas. Overturf et al. (Human Gene Ther. 9:295, 1998) have developed a model for Hereditary Tyrosinemia Type I in mice by targeted disruption of the Fah gene. The animals can be rescued from the deficiency by providing a supply of 2-(2-nitro-4-fluoro-methyl-benzyol)-1,3-cyclohexanedione (NTBC), but develop liver disease when NTBC is withdrawn. Acute liver disease can be modeled by 90% hepatectomy (Kobayashi et al., Science 287:1258, 2000). Acute liver disease can also be modeled by treating animals with a hepatotoxin such as galactosamine, $CCl_4$, or thioacetamide. Chronic liver diseases such as cirrhosis can be modeled by treating animals with a sublethal dose of a hepatotoxin long enough to induce fibrosis (Rudolph et al., Science 287:1253, 2000). Assessing the ability of differentiated cells to reconstitute liver function involves administering the cells to such animals, and then determining survival over a 1 to 8 week period or more, while monitoring the animals for progress of the condition. Effects on hepatic function can be determined by evaluating markers expressed in liver tissue, cytochrome p450 activity, and blood indicators, such as alkaline phosphatase activity, bilirubin conjugation, and prothrombin time), and survival of the host Any improvement in survival, disease progression, or maintenance of hepatic function according to any of these criteria relates to effectiveness of the therapy, and can lead to further optimization.

This invention includes differentiated cells that are encapsulated, or part of a bioartificial liver device. Various forms of encapsulation are described in "Cell Encapsulation Technology and Therapeutics", Kuhtreiber et al. eds., Birkhauser, Boston Mass., 1999. Differentiated cells of this invention can be encapsulated according to such methods for use either in vitro or in vivo.

Bioartificial organs for clinical use are designed to support an individual with impaired liver function—either as a part of long-term therapy, or to bridge the time between a fulminant hepatic failure and hepatic reconstitution or liver transplant. Bioartificial liver devices are reviewed by Macdonald et al., pp. 252-286 of "Cell Encapsulation Technology and Therapeutics", op cit., and exemplified in U.S. Pat. Nos. 5,290,684, 5,624,840, 5,837,234, 5,853,717, and 5,935,849. Suspension-type bioartificial livers comprise cells suspended in plate dialysers, or microencapsulated in a suitable substrate, or attached to microcarrier beads coated with extracellular matrix. Alternatively, hepatocytes can be placed on a solid support in a packed bed, in a multiplate flat bed, on a microchannel screen, or surrounding hollow fiber capillaries. The device has inlet and outlet through which the subject's blood is passed, and sometimes a separate set of ports for supplying nutrients to the cells.

Current proposals for such liver support devices involve hepatocytes from a xenogeneic source, such as a suspension of porcine hepatocytes, because of the paucity of available primary human hepatocytes. Xenogeneic tissue sources raise regulatory concerns regarding immunogenicity and possible cross-species viral transmission.

The present invention provides a system for generating preparative cultures of human cells. Differentiated pluripotent stem cells are prepared according to the methods described earlier, and then plated into the device on a suitable substrate, such as a matrix of Matrigel® or collagen. The efficacy of the device can be assessed by comparing the composition of blood in the afferent channel with that in the efferent channel—in terms of metabolites removed from the afferent flow, and newly synthesized proteins in the efferent flow.

Devices of this kind can be used to detoxify a fluid such as blood, wherein the fluid comes into contact with the differentiated cells of this invention under conditions that permit the cell to remove or modify a toxin in the fluid. The detoxification will involve removing or altering at least one ligand, metabolite, or other compound (either natural and synthetic) that is usually processed by the liver. Such compounds include but are not limited to bilirubin, bile acids, urea, heme, lipoprotein, carbohydrates, transferrin, hemopexin, asialoglycoproteins, hormones like insulin and glucagon, and a variety of small molecule drugs. The device can also be used to enrich the efferent fluid with synthesized proteins such as albumin, acute phase reactants, and unloaded carrier proteins. The device can be optimized so that a variety of these functions are performed, thereby restoring as many hepatic functions as are needed. In the context of therapeutic care, the device processes blood flowing from a patient in hepatocyte failure, and then the blood is returned to the patient.

Differentiated pPS cells of this invention that demonstrate desirable functional characteristics in animal models (such as those described above) may also be suitable for direct administration to human subjects with impaired liver function. For purposes of hemostasis, the cells can be administered at any site that has adequate access to the circulation, typically within the abdominal cavity. For some metabolic and detoxification functions, it is advantageous for the cells to have access to the biliary tract. Accordingly, the cells are administered near the liver (e.g., in the treatment of chronic liver disease) or the spleen (e.g., in the treatment of fulminant hepatic failure). In one method, the cells administered into the hepatic circulation either through the hepatic artery, or through the portal vein, by infusion through an indwelling catheter. A catheter in the portal vein can be manipulated so that the cells flow principally into the spleen, or the liver, or a combination of both. In another method, the cells are administered by placing a bolus in a cavity near the target organ, typically in an excipient or matrix that will keep the bolus in place. In another method, the cells are injected directly into a lobe of the liver or the spleen.

The differentiated cells of this invention can be used for therapy of any subject in need of having hepatic function restored or supplemented. Human conditions that may be appropriate for such therapy include fulminant hepatic failure due to any cause, viral hepatitis, drug-induced liver injury, cirrhosis, inherited hepatic insufficiency (such as Wilson's disease, Gilbert's syndrome, or $\alpha_1$-antitrypsin deficiency), hepatobiliary carcinoma, autoimmune liver disease (such as autoimmune chronic hepatitis or primary biliary cirrhosis), and any other condition that results in impaired hepatic function. For human therapy, the dose is generally between about $10^9$ and $10^{12}$ cells, and typically between about $5 \times 10^9$ and $5 \times 10^{10}$ cells, making adjustments for the body weight of the subject, nature and severity of the affliction, and the replicative capacity of the administered cells. The ultimate responsibility for determining the mode of treatment and the appropriate dose lies with the managing clinician.

The following examples provided as further non-limiting illustrations of particular embodiments of the invention.

EXAMPLES

Experimental Procedures

This section provides details of some of the techniques and reagents used in the Examples below.

Maintenance of Human Embryonic Stem Cells:

hES cells were maintained on primary mouse embryonic fibroblasts in serum-free media. The hES cells were seeded as small clusters on irradiated mouse embryonic fibroblasts at about 40,000 cells cm$^{-2}$. These cultures were maintained in a medium composed of 80% KO DMEM (Gibco) and 20% Serum Replacement (Gibco), supplemented with 1% non-essential amino acids, 1 mM glutamine, 0.1 mM β-mer- captoethanol and 4 ng/mL human bFGF (Gibco). Cells were expanded by serial passaging of the ES colonies. This was accomplished by treating the monolayer culture of ES colonies with 1 mg/mL collagenase for 5-20 minutes at 37° C. The cultures were then gently scraped to remove the cells. The clusters were gently dissociated, and replated as small clusters onto fresh feeder cells.

Production of Embryoid Bodies (EB)

Confluent monolayer cultures of hES cells on or off feeder cells were harvested by incubating in collagenase for 15-20 min, following which the cells are scraped from the plate. The cells were then dissociated into clusters and plated in non-adherent cell culture plates (Costar) in a medium composed of 80% KO DMEM (Gibco) and 20% non-heat-inactivated FBS (Hyclone), supplemented with 1% non-essential amino acids, 1 mM glutamine, 0.1 mM β-mercaptoethanol. The cells were seeded at a 1:2 ratio in 2 mL medium per well (6 well plate). The EBs were fed every other day by the addition of 2 mL of medium per well. When the volume of medium exceeded 4 mL/well, the EBs were collected and resuspended in fresh medium. After 4-8 days in suspension, the EBs were plated onto a substrate and allowed to differentiate further.

Matrigel® Coated Culture Substrates

Wells were coated with Matrigel® according to manufacturer's directions. Briefly, either regular Matrigel® or growth factor reduced Matrigel® (Collaborative Biosciences) was thawed at 4° C. for at least 3 h. It was diluted 1:10 or 1:20 in cold KO DMEM for hES cell cultures or 1:30 for hepatocyte cultures. Using pre-cooled plates and pipette tips 0.75-1 mL of Matrigel solution was added to each well (9.6 cm$^2$). The plate was incubated at room temperature for one h or at 4° C. overnight, and then washed once with cold KO DMEM before adding cells.

Immunocytochemistry

Cells growing on chamber slides were fixed in 3.5% paraformaldehyde for 5 min at room temperature, and then for 20 minutes in methanol at −20° C. The fixed cells were rinsed with PBS twice and blocked for 1 hour in 10% goat serum in PBS. They were then incubated in primary antibody diluted in 10% goat serum and PBS for 2 h. Antibody to albumin, alpha fetoprotein (AFP) (Sigma) and $\alpha_1$-antitrypsin (OEB Biosciences Inc.) were diluted at 1:500, cytokeratin, 8, 18 and 19, desmin, (Neomarkers), vimentin (Dako) and SMA (Sigma) were diluted at 1:200. Cells were then washed 3 times with PBS and incubated in secondary antibody, which was FITC-conjugated anti-mouse IgG diluted 1:100 and Hoechst HH33258 (Sigma) at 1:1000 in 5% goat serum in PBS, and incubated for 1 h. The stained cells were then washed 3 times in PBS, and mounted in Vectashield™ (Vector Labs). Images were taken at 10× and 40× using a Nikon Labophot™ equipped with epifluorescence and a spot CCD camera.

Glycogen Staining

Periodic Acid Schiff's stain (PAS) was obtained from American Master Tech Scientific Inc. Cells were grown on chamber slides and fixed in acetone:methanol 1:1 at 20° C. for 20 min. The fixed cells were rinsed in tap water followed by distilled water. The cells were then incubated in 0.5% periodic acid solution for 4 min at room temperature, and rinsed with distilled water. They were then incubated with Schiff's solution for 10 min at room temperature and rinsed with tap water several times. The cells were then incubated in Fast Green stain for 2 minutes, rinsed twice with 100% alcohol, and mounted in DPX mounting media. Images were taken at 10× and 40× using Nikon Labophot™ equipped with epifluorescence and a spot CCD camera.

BrdU Staining

Cells were grown on chamber slides in the indicated growth medium, and labeled with 10 µM BrdU for 24 h. Cells were then fixed with 3:1 methanol: acetic acid for 30 minutes, and air-dried overnight in the dark. The fixed cells were rinsed once in PBS, and denatured in 0.07 N NaOH for 2 min followed by quick rinses in PBS pH 8.5 and pH7.4 several times. They were then blocked using 1.5% goat serum (Vector Labs) for 15 min, and incubated with anti BrdU antibody (Sigma) diluted 1:500 in 1.5% goat serum and 0.05% Tween™ 20 for 2 h. The samples were washed thrice in PBS, and then incubated with secondary antibody, which was biotinylated goat anti-mouse immunoglobulin (Vector Labs), at 10 µg/mL diluted in 1.5% horse serum for 30 min. The sample was washed again thrice in PBS, and then incubated with the staining conjugate, Texas Red labeled streptavidin (Vector Labs) at 30 µg/mL diluted in 10 mM HEPES buffer and 0.15M NaCl pH 8.5, for 20 min in the dark. Hoechst HO33258 stain (bisbenzimide, Sigma Cat. No. B2883) was mixed into the streptavidin solution at 2.5uM final concentration to stain all the nuclei. The stained cells were washed again 3× in PBS, and mounted in Vectashield™ (Vector Labs). Images were taken at 10× and 40× using Nikon Labophot™ equipped with epifluorescence and a spot CCD camera.

Reverse-transcriptase PCR Amplification

RT-PCR analysis of expression at the transcription level was conducted as follows: RNA was extracted from the cells using RNAeasy Kit™ (Qlagen) as per manufacturer's instructions. The final product was then digested with DNase to get rid of contaminating genomic DNA. The RNA was incubated in RNA guard (Pharmacia Upjohn) and DNAse I (Pharmacia Upjohn) in buffer containing 10 mM Tris pH 7.5, 10 mM MgCl$_2$, and 5 mM DDT at 37° C. for 30-45 minutes. To remove protein from the sample, phenol chloroform extraction was performed and the RNA precipitated with 3 M sodium acetate and 100% cold ethanol. The RNA was washed with 70% ethanol, and the pellet was air-dried and resuspended in DEPC-treated water. For the reverse transcriptase (RT) reaction, 500 ng of total RNA was combined with a final concentration of 1×First Strand Buffer (Gibco), 20 mM DDT and 25 µg/mL random hexamers (Pharmacia Upjohn). The RNA was denatured for 10 min at 70° C., followed by annealing at room temperature for 10 min. dNTPs were added at a final concentration of 1 mM along with 0.5 µL of Superscript II RT (Gibco), incubated at 42° C. for 50 minutes, and then heat-inactivated at 80° C. for 10 min. Samples were then stored at −20° C. till they were processed for PCR analysis. Standard polymerase chain reaction (PCR) was performed using primers specific for the markers of interest in the following reaction mixture: cDNA 1.0 µL, 10×PCR buffer (Gibco) 2.5 µL, 10×MgCl$_2$ 2.5 µL, 2.5 mM dNTP 3.0 µL, 5 µM 3'-primer 1.0 µL, 5 µM 5'-primer, 1.0 µL, Taq 0.4 µL, DEPC-water 13.6 µL. Selected markers and reaction conditions are shown in Table 3.

TABLE 3

Reaction Conditions for Expression Analysis by RT-PCR

| Marker | Expected size | McCl$_2$ (mM) | Annealing temp | PCR Cycle |
| --- | --- | --- | --- | --- |
| α-fetoprotein | 157 | 1.75 | 59° C. | (94° C. 30 sec; 59° C. 30 sec; 72° C. 30 sec) × 30 |
| albumin | 233 | 1.5 | 57° C. | (94° C. 30 sec; 57° C. 30 sec; 72° C. 30 sec) × 35 |
| α$_1$-antitrypsin | 213 | 1.5 | 67° C. | (94° C. 30 sec; 57° C. 30 sec; 72° C. 30 sec) × 35 |
| HNF1a | 150 | 1.5 | 62° C. | (94° C. 3 min) × 1; (94° C. 30 sec; 62° C. 30 sec; 72° C. 30 sec) × 35; (72° C. 10 min) × 1 |
| HNF3β | 170 | 1.5 | 62° C. | (94° C. 3 min) × 1; (94° C. 30 sec; 62° C. 30 sec; 72° C. 30 sec) × 35; (72° C. 10 min) × 1 |
| HNF4a | 497 | 1.5 | 61° C. | (94° C. 3 min) × 1; (94° C. 30 sec; 61° C. 30 sec; 72° C. 30 sec) × 35; (72° C. 10 min) × 1 |
| ASGR | 226 | 1.5 | 60° C. | (94° C. 3 min) × 1; (94° C. 30 sec; 60° C. 30 sec; 72° C. 30 sec) × 35; (72° C. 10 min) × 1 |
| GATA4 | 256 | 1.25 | 62–70° C. | (94° C. 30 sec; 70° C. 30 sec) × 35 |
| C/EBPα | 396 | 1.5 | 61° C. | (94° C. 3 min) × 1; (94° C. 30 sec; 61° C. 30 sec; 72° C. 30 sec) × 35; (72° C. 10 min) × 1 |
| C/EBPβ | 213 | 1.5 | 61° C. | (94° C. 3 min) × 1; (94° C. 30 sec; 61° C. 30 sec; 72° C. 30 sec) × 35; (72° C. 10 min) × 1 |
| β-actin (control) | 285 | 1.5–2.5 | 55–61° C. | any cycle above |

Example 1

Differentiation of Human Embryonic Stem Cells Using n-butyrate

Embryoid bodies (EB) were prepared as described in the preceding section. After 5 days in suspension culture, they were harvested and plated on Growth Factor Reduced Matrigel® coated plates and in chamber slides (Nunc). One of the following three conditions was used in parallel:

medium containing 20% fetal bovine serum (FBS);
medium containing 20% FBS and 5 mM sodium butyrate (Sigma);
medium containing 20% FBS, 0.5% DMSO (ATCC), 4 µM dexamethazone (Sigma), 150 ng/ml insulin, 10 ng/ml EGF, 600 nM glucagon (Sigma).

In each case, the medium was exchanged every day, and cells were fixed for immunocytochemistry on day 4 after plating.

One day after plating, the EBs plated in 20% FBS alone looked healthy, almost all of them adhered to the plate and appeared to be proliferating. After several days, the cells in FBS alone survived well, and differentiated to form a very heterogeneous population. In contrast, 1 day after plating the cultures containing sodium butyrate had a large proportion of apparently dead cells, and only some patches comprising a fairly homogenous population of cells survived. The morphology of these cells was similar to that of primary hepatocytes, in that the cells were large and became multi-nucleated after a few days. These cultures were compared with cultures of primary human hepatocytes (obtained from Dr. Stephen Strom, University of Pittsburgh), and with HepG2 cells (a permanent human hepatocyte cell line derived from a hepatoblastoma, similar to what is reported in U.S. Pat. No. 5,290,684). In the condition with 0.5% DMSO and growth factors (no. 3), the cells looked healthy and the cultures contained a remarkably heterogeneous population of cells.

FIG. 1 shows the morphology of embryoid body cells replated and cultured for a further 2 days (4×, 10×, 20×). The right side shows cells differentiated by culturing 2 days in the hepatocyte differentiation agent n-butyrate. A round colony forms at the site where an embryoid body is plated; the white patch in the middle is a small region of dead cells. The other cells in the field show remarkably homogenous morphology. The left side shows cells cultured in serum-containing medium alone. The embryoid body disperses over a wide area, and forms heterogeneous patches of cells that show the morphology of many different cell types.

Four days after plating, cells growing on chamber slides were fixed for immunocytochemistry, using antibodies against different liver specific markers. Results are shown in Table 4. Cultures treated with sodium butyrate did not express AFP, but about 30% of the cells expressed antibody-detectable levels of albumin.

TABLE 4

Immunocytochemistry of Cultured Cells

| specificity of primary antibody | Embryonic Stem Cells cultured 4 days with | | | primary human hepatocytes |
|---|---|---|---|---|
| | Na butyrate | FBS alone | FBS + DMSO | |
| (none) | — | – | – | — |
| non-specific IgG1 | — | – | – | — |
| AFP | — | + | + | — |
| Albumin | 30% + ve* | – | – | 100% + ve |
| $\alpha_1$-antitrypsin | >60% + ve | + | + | >80% + ve |
| CK18 | 100% + ve | + | + | 100% + ve |
| CK8 | 100% + ve | + | + | 100% + ve |
| CK19 | 100% + ve | + | + | 100% + ve |
| Desmin | — | 5% + ve | 5% + ve | (n.d.) |
| Vimentin | 100% + ve | + | + | 100% + ve |
| SMA | <1% + ve | 20% + ve | 5% + ve | (n.d.) |

*results are given in terms of percentage of cells showing positive staining
(n.d.) = not determined in this experiment Example 2

Markers Expressed by Differentiated Cells hES cell derived embryoid bodies were harvested after 4 or 5 days in suspension, and plated on Matrigel® coated 6-well plates (for RNA extraction) and chamber slides (for immunocytochemistry) in medium containing 20% FBS and 5 mM sodium n-butyrate. The medium was changed daily or every other day. There was a lot of cell death on day 1 followed by less cell death on the subsequent days.

FIG. 2 shows the morphology of the differentiated cells after 6 days of culture with n-butyrate. Six different fields are shown from the same culture (10× in the top row, 20× in the other rows). The cells are remarkably uniform, showing a large polygonal surface and binucleated center characteristic of mature hepatocytes.

On the sixth day after plating in the differentiation agent, the cells were analyzed for expression of markers by RT-PCR and immunocytochemistry, following the procedures outlined earlier. Glycogen content in these cells was determined using periodic acid Schiff stain. The number of cells in S phase of cell cycle was determined by incubating the cells with 10 μM BrdU on day 5 after plating, and subsequently staining with anti-BrdU antibody 24 hours later.

FIG. 3 shows the results of immunohistochemical staining for certain cell specific markers. FIG. 3A (40×) shows the results for primary adult human hepatocytes obtained from the University of Pittsburgh—antibody staining on the right side, Hoechst HH33258 bisbenzimide staining of the same field for cell nuclei on the left side. FIG. 3B (20×) shows the results for hES cells cultured 6 days with n-butyrate. Both sets of cells show staining in a high proportion of cells for albumin, $\alpha_1$-antitrypsin, and CD18, three markers characteristic of cells of the hepatocyte lineage, and negative for α-fetoprotein which is a marker for early progenitor cells.

FIG. 4 shows the glycogen staining pattern of cells cultured 6 days in n-butyrate (10× and 40×). The cells were stained with Periodic Acid Schiff's stain for glycogen (pink, dark color) and with Fast Green stain to outline the cell cytoplasm (background green, light color). About 60% of the butyrate treated cells show evidence of glycogen storage (top row), compared with 80% in fetal hepatocytes (middle row, positive control) and virtually none in the human fibroblast cell line designated BJ fibroblast (bottom row, negative control).

A summary of the phenotype analysis is provided in Table 5. Albumin expression was found in 55% of the cells. AFP was completely absent. Glycogen was being stored in at least 60% of the cells. 16% of the cells labeled with BrdU, indicating that a significant portion of the cells were proliferating at the time of analysis.

TABLE 5

Phenotype of Differentiated Cells

| Primary Antibody Specificity | % positive cells |
|---|---|
| (none) | 0 |
| non-specific IgG1 | 0 |
| α-fetoprotein | 0 |
| Albumin | 55% |
| $\alpha_1$-antitrypsin | 90% |
| CK18 | 100% |
| CK8 | 100% |
| CK19 | 100% |
| Desmin | 0 |
| Glycogen staining | 60% |
| BrdU staining | 16% |

RT-PCR analysis was also performed after six days of culture with n-butyrate to look at the expression pattern of various genes normally expressed in hepatocytes. These data were compared with the expression pattern of the same genes in adult hepatocytes, fetal hepatocytes, HepG2 cells (a hepatocarcinoma line) and a non hepatocyte RPE (Retinal pigment epithelial) cell line. Results are shown in Table 6.

TABLE 6

RTPCR analysis of Gene Expression

| | HepG2 hepatocyte cell line (positive control) | primary human hepatocytes (positive control) | primary fetal hepatocytes (positive control) | hES cells (undifferentiated) | Embryoid Body cells cultured in FBS (cell mixture) | Embryoid Body cells cultured with DMSO and growth factors | Embryoid Body cells cultured with sodium n-butyrate | RPE epithelial cell line (negative control) |
|---|---|---|---|---|---|---|---|---|
| β-actin | + | + | + | + | + | + | + | + |
| α-fetoprotein | + | + | + | + | + | + | + | − |
| albumin | + | + | + | − | + | + | + | − |
| α$_1$-antitrypsin | + | + | + | − | + | + | + | + |
| HNF1a | + | + | + | − | + | + | − | − |
| HNF3b | + | + | + | − | + | + | − | − |
| HNF4a | + | + | + | − | − | − | − | − |
| ASG receptor | + | + | + | − | + | + | + | − |
| GATA-4 | + | + | + | + | + | + | + | − |
| C/EBPα | + | + | + | − | + | + | + | − |
| C/EBPβ | + | + | + | − | + | + | + | − |

The effect of sodium butyrate was compared with other potential hepatocyte differentiation agents in a similar protocol. Embryoid bodies were cultured in suspension for 4 days, and then replated on plates coated with collagenase 1. The cells were then cultured in the presence of each compound for 6 days. Results are shown in Table 7.

TABLE 7

Hepatocyte Differentiation Agents

| | Induction of hepatocyte phenotype |
|---|---|
| NaCl | − |
| n-Butyric Acid | + |
| Sodium n-butyrate | + |
| α-hydroxybutyric acid | − |
| β-hydroxybutyric acid | − |
| Propionic acid | ± |
| Valeric acid | − |
| Isovaleric acid | ± |
| Caproic acid | − |
| Isobutyric acid | ± |
| Trichostatin A | + |

+ Causes hepatocyte differentiation and selective elimination of other cell types
− No inductive effect
± Mild inductive effect; may allow growth or survival of other cell types At a concentration of 5 mM, sodium chloride had no effect, while butyric acid and sodium butyrate were equally effective—indicating that the differentiation is not simply due to a change in ion concentration. The reader will appreciate that butyric acid and [sodium] butyrate are conjugate forms of the same substance that are within the buffering capacity of culture media. Accordingly, the terms are interchangeable in this disclosure unless explicitly required otherwise.

For comparative purposes, a variety of structural analogs of butyrate were tested at 5 mM. The analogs propionic acid, isovaleric acid, and isobutyric acid were effective in causing hepatocyte differentiation, but were deemed less preferable under these conditions because enrichment for cells bearing the hepatocyte phenotype was less robust.

Trichostatin A, which is another inhibitor for histone deacetylase, was found to be toxic to cells in the range of 2.5-100 μM, and ineffective at 10-50 nM. At 75-100 nM, Trichostatin A appeared to both induce hepatocyte differentiation and select against survival of other cell types. The phenotype of hepatocyte lineage cells made using 5 mM sodium n-butyrate and 100 nM Trichostatin A is shown in Table 8.

TABLE 8

Phenotype of Differentiated Cells

| Primary Antibody Specificity | hES cells differentiated using Sodium Butyrate | hES cells differentiated using Trichostatin A | primary human hepatocytes |
|---|---|---|---|
| (none) | 0% | | 0% |
| non-specific IgG1 | 0% | | 0% |
| α-fetoprotein | 0% | | 0% |
| albumin | 62% | 41% | >80% |
| α$_1$-antitrypsin | 90% | 81% | 90% |
| CK18 | 100% | >70% | 100% |
| CK19 | 100% | >90% | 100% |
| Glycogen staining | >60% | >50% | >80% |

Example 3

Augmentation of the Differentiating Effect of n-butyrate with Hepatocyte Maturation Factors The effect of various possible hepatocyte maturation factors was tested in cells differentiated using n-butyrate. hES were cultured for 4 days in 5 mM sodium n-butyrate, and then switched to a different medium. The following alternatives were tested:

1. "HCM" medium from Clonetics
2. 10% fetal bovine serum (FBS) supplemented with insulin, epidermal growth factor (EGF), dexamethazone, and glucagon;
3. 10% calf serum (CS) supplemented with insulin, EGF, dexamethazone, and glucagon;
4. 20% FBS supplemented with insulin, EGF, dexamethazone, and glucagon The cells were maintained under these conditions for 4 days. Cells survived under all conditions, but appeared best in 10% FBS with growth factors (Groups 2 and 4). These cells were trypsinized and replated in fresh Matrigel® coated plates. Other growth factors are tested in a similar protocol, or in combination, to determine their effects on hepatocyte maturation and cell phenotype.

Example 4

Telomerization of hES-derived Hepatocytes

Several days after differentiation of hES with sodium butyrate, cells are transduced with a retrovirus encoding the human homolog of telomerase reverse transcriptase (hTERT). The vector comprises an hTERT encoding sequence from a plasmid designated pGRN145, into the EcoR1 site of the commercially available pBABE puromycin construct. The hTERT encoding sequence is placed under control of the retrovirus LTR promoter. Control and hTERT pBABE retroviral supernatants are prepared using the PA317 packaging cell line, and combined with 4 µg/mL polybrene.

Cultures of differentiated hES cells are prepared, and the medium is replaced with a medium containing retrovirus supernatant for 8-16 hours. The medium is replaced again with normal growth medium, and the cells are allowed to recover for 1-2 days. Cells are then selected using 0.5-2.5 µg/mL puromycin.

The cells are evaluated morphologically, for growth rate, and for expression patterns using immunocytochemistry and RT-PCR. Telomerase activity is evaluated using the TRAP assay.

Example 5

Differentiation of Human Embryonic Stem Cells in Feeder-free Culture

Undifferentiated hES colonies were passaged continuously in feeder-free conditions as follows. Cultures were incubated in 1 mg/mL collagenase for about 5 minutes at 37° C. The cells were then harvested by scraping the cells off the surface and dissociating them into small clumps. Cells were split at a 1:3 or 1:6 ratio, ~55,000 cells/mL (17,000 cells/cm$^2$). The day after replating, colonies of undifferentiated cells could again be identified. Single cells in between the colonies were differentiated. Over the next few days, the undifferentiated cells were seen to proliferate and the colonies became large and compact. The differentiated cells in between the colonies also became more compact. The cells became confluent after 4-7 days of being fed daily with conditioned media. When the cells reached confluence, they were split once more.

For this example, the H9 hES cells (p30+5) were maintained in feeder-free conditions for 30 days (5 passages) before differentiation. The undifferentiated cells were maintained on laminin and fed with MEF-conditioned medium, as described elsewhere in this disclosure. To induce differentiation, the conditioned medium was replaced with SR medium (without supplemental bFGF) containing 5 mM sodium butyrate.

After one day in these conditions, small patches of cells could be seen that had a hepatocyte-like morphology. In addition, a large number of cells died and appeared to be adhered to the bottom of the dish. In the control cultures that received SR media without butyrate, considerable diversity of differentiation (cells with different morphologies) was observed. About six days after treatment, the culture that had received sodium butyrate contained many patches of hepatocyte-like cells, but a few cells with other morphologies were identified. Many dead cells still adhered to the dish. Cultures that did not receive butyrate appeared very differentiated, with a diversity of phenotypes.

In subsequent experiments, hES cells maintained in feeder-free conditions are exposed to sodium butyrate at the time of passaging. The hES cell line designated H9 and maintained for 48 days (8 passages) on Matrigel® is harvested at confluence using collagenase, and reseeded on Matrigel®. The cells are passaged into SR media containing 5 mM sodium butyrate, and assessed for hepatocyte-like morphology and gene expression at various times of culture, in comparison with cells cultured without butyrate.

Example 6

Effect of Butyrate in Combination With DMSO

In this experiment, the effect of the hepatocyte differentiation agent butyrate was determined in the presence of hepatocyte maturation factor DMSO.

Human ES cell derived embryoid bodies were harvested after 4 days in suspension and plated in the following four conditions.

Gelatin coated plates in the presence of 5 mM Na butyrate

Gelatin coated plates in the presence of 5 mM Na butyrate and 1% DMSO

Matrigel® coated plates in the presence of 5 mM Na butyrate.

Matrigel® coated plates in the presence of 5 mM Na butyrate and 1% DMSO

Media were changed every other day and cells were analyzed on day 7 for immunocytochemistry and RT-PCR. Cells in all these conditions looked morphologically alike, comprising colonies of cells with uniform morphology. There were fewer colonies of cells in the set where butyrate and DMSO were both present, compared with the ones cultured in butyrate alone. The two sets that were plated on gelatin had even less cells.

Immunostaining showed a similar marker phenotype in all the conditions. Percentage of cells in the culture staining for each of the markers tested is shown in Table 9.

TABLE 9

Phenotype of Differentiated Cells

|  | Group 1<br>Gelatin<br>Butyrate | Group 2<br>Gelatin<br>Butyrate + DMSO | Group 3<br>Matrigel ®<br>Butyrate | Group 4<br>Matrigel ®<br>Butyrate + DMSO |
|---|---|---|---|---|
| No Primary antibody | 0 | 0 | 0 | 0 |
| IgG1 | 0 | 0 | 0 | 0 |
| α-fetoprotein | 0 | 0 | 0 | 0 |
| Albumin | 56% | 75% | 50% | 63% |
| α$_1$-antitrypsin | >90% | >90% | >90% | >90% |

TABLE 9-continued

| | Phenotype of Differentiated Cells | | | |
|---|---|---|---|---|
| | Group 1 Gelatin Butyrate | Group 2 Gelatin Butyrate + DMSO | Group 3 Matrigel ® Butyrate | Group 4 Matrigel ® Butyrate + DMSO |
| CK18 | 100% | 100% | 100% | 100% |
| CK19 | 100% | 100% | 100% | 100% |
| Glycogen | >60% | >60% | >60% | >60% |

Example 7

Direct Differentiation of hES to Hepatocyte-like Cells Without Forming Embryoid Bodies The undifferentiated hES cells were maintained in feeder-free conditions (on Matrigel® in MEF-CM). The strategy was to initiate a global differentiation process by adding the hepatocyte maturation factors DMSO or retanoic acid (RA) to a subconfluent culture. The cells are then induced to form hepatocyte-like cells by the addition of Na-butyrate.

The hES cells were maintained in undifferentiated culture conditions for 2-3 days after splitting. At this time, the cells were 50-60% confluent and the medium was exchanged with unconditioned SR medium containing 1% DMSO. The cultures were fed daily with SR medium for 4 days and then exchanged into unconditioned SR medium containing 2.5% Na-butyrate. The cultures were fed daily with this medium for 6 days; at which time one half of the cultures were evaluated by immunocytochemistry. The other half of the cultures were harvested with trypsin and replated onto collagen, to further promote enrichment for hepatocyte lineage cells. Immunocytochemistry was then performed on the following day.

As shown in Table 10, the cells which underwent the final re-plating had ~5-fold higher albumin expression, similar $\alpha_1$-antitrypsin expression and 2-fold less cytokeratin expression than the cells not re-plated. The secondary plating for the cells is believed to enrich for the hepatocyte-like cells.

TABLE 10

| | Phenotype of Differentiated Cells | |
|---|---|---|
| Antibody Specificity | No trypsinization % positive | Trypsinization % positive |
| (no primary antibody) | 0 | 0 |
| (IgG1 control) | 0 | 0 |
| albumin | 11% | 63% |
| $\alpha_1$-antitrypsin | >80% | >80% |

TABLE 10-continued

| | Phenotype of Differentiated Cells | |
|---|---|---|
| Antibody Specificity | No trypsinization % positive | Trypsinization % positive |
| $\alpha$-fetoprotein | 0 | 0 |
| Cytokeratin 8 | >80% | 45% |
| Cytokeratin 18 | >80% | 30% |
| Cytokeratin 19 | >80% | 30% |
| glycogen | 0 | >50% |

Example 8

Comparison of Different Matrices for Hepatocyte Differentiation from hES Cells

EBs were generated from hES cells in feeder-free conditions. After 4 days in suspension, the EBs were plated in 20% FBS medium supplemented with 5 mM Na-butyrate or 5 mM Na-butyrate and 1% DMSO. The EBs were plated on the following matrices:

1. collagen I (0.03 mg/mL coated overnight at 37° C.)
2. growth factor reduced Matrigel® (1:10, coated for 1 h at room temp)
3. gelatin (1% coated for 2 h at 37° C.)

After 6 days in Na-butyrate the cells were evaluated morphologically and using immunocytochemistry for hepatocyte markers. In all conditions, homogeneous patches of hepatocyte-like cells were observed. However, the number of cell clusters was greatly reduced in the cultures with gelatin coating compared with other conditions. As shown in Table 11, the percentage of cells with albumin, cytokeratin, and $\alpha_1$-antitrypsin immunoreactivity was similar in all conditions. Glycogen storage was also similar in all conditions. These data indicate that all the substrates tested promote hepatocyte differentiation, but Matrigel® and collagen I coating support survival better than gelatin.

TABLE 11

| | Phenotype of Differentiated Cells | | | | | |
|---|---|---|---|---|---|---|
| | Matrigel ® | | Gelatin | | Collagen I | |
| Antibody Specificity | Butyrate | Butyrate + DMSO | Butyrate | Butyrate + DMSO | Butyrate | Butyrate + DMSO |
| (no primary) | 0 | 0 | 0 | 0 | 0 | 0 |
| (IgG1 control) | 0 | 0 | 0 | 0 | 0 | 0 |
| $\alpha$-fetoprotein | 0 | 0 | 0 | 0 | 0 | 0 |
| albumin | 56% | 75% | 50% | 63% | 79% | 75% |
| $\alpha_1$-antitrypsin | >90% | >90% | >90% | >90% | >90% | >90% |

TABLE 11-continued

Phenotype of Differentiated Cells

| | Matrigel ® | | Gelatin | | Collagen I | |
|---|---|---|---|---|---|---|
| Antibody Specificity | Butyrate | Butyrate + DMSO | Butyrate | Butyrate + DMSO | Butyrate | Butyrate + DMSO |
| Cytokeratin 18 | 100% | 100% | 100% | 100% | 100% | 100% |
| Cytokeratin 19 | 100% | 100% | 100% | 100% | 100% | 100% |
| Glycogen | >60% | >60% | >60% | >60% | >60% | >60% |

Example 9
Further Optimization of Conditions for Direct Differentiation hES cells undergo the Direct Differentiation protocol detailed earlier, making the adjustments to culture conditions shown in Table 12. Hepatocyte Culture Medium is purchased from Clonetics; Strom's Medium is prepared as described in Runge et al., Biochem. Biophys. Res. Commun. 265:376, 1999. The cell populations obtained are assessed by immunocytochemistry and enzyme activity.

TABLE 12

Direct Differentiation Protocols

| Protocol No. | Stage I Undifferentiated cells (until confluent) | Stage II Pre-differentiation (4 days) | Stage III Hepatocyte differentiation (6 days) | Stage IV Hepatocyte maturation (Groups 7–9 only; 4 days) |
|---|---|---|---|---|
| 1 | Feeder-free conditions | 20% SR medium + 1% DMSO | HCM + 30 ng/mL hEGF + 10 ng/mL TGF-α + 30 ng/mL HGF + 1% DMSO + 2.5 mM butyrate | |
| 2 | Feeder-free conditions | 20% SR medium + 1% DMSO | 20% SR medium + 30 ng/mL hEGF + 10 ng/mL TGF-α + 30 ng/mL HGF + 1% DMSO + 2.5 mM butyrate | |
| 3 | Feeder-free conditions | 20% SR medium + 1% DMSO | Strom's medium + 30 ng/mL hEGF + 10 ng/mL TGF-α + 30 ng/mL HGF + 1% DMSO + 2.5 mM butyrate | |
| 4 | Feeder-free conditions | HCM + 30 ng/mL hEGF + 10 ng/mL TGF-α + 30 ng/mL HGF + 1% DMSO | HCM + 30 ng/mL hEGF + 10 ng/mL TGF-α + 30 ng/mL HGF + 1% DMSO + 2.5 mM butyrate | |
| 5 | Feeder-free conditions | 20% SR medium + 30 ng/mL hEGF + 10 ng/mL TGF-α + 30 ng/mL HGF + 1% DMSO | 20% SR medium + 30 ng/mL hEGF + 10 ng/mL TGF-α + 30 ng/mL HGF + 1% DMSO + 2.5 mM butyrate | |
| 6 | Feeder-free conditions | Strom's medium + 30 ng/mL hEGF + 10 ng/mL TGF-α + 30 ng/mL HGF + 1% DMSO | Strom's medium + 30 ng/mL hEGF + 10 ng/mL TGF-α + 30 ng/mL HGF + 1% DMSO + 2.5 mM butyrate | |
| 7 | Feeder-free conditions | 20% SR medium + 1% DMSO | 20% SR medium + 1% DMSO + 2.5 mM butyrate | HCM + 30 ng/mL hEGF + 10 ng/mL TGF-α + 30 ng/mL HGF + 1% DMSO + 2.5 mM butyrate |
| 8 | Feeder-free conditions | 20% SR medium + 1% DMSO | 20% SR medium + 1% DMSO + 2.5 mM butyrate | 20% SR medium + 30 ng/mL hEGF + 10 ng/mL TGF-α + |

TABLE 12-continued

Direct Differentiation Protocols

| Protocol No. | Stage I Undifferentiated cells (until confluent) | Stage II Pre-differentiation (4 days) | Stage III Hepatocyte differentiation (6 days) | Stage IV Hepatocyte maturation (Groups 7–9 only; 4 days) |
|---|---|---|---|---|
| 9 | Feeder-free conditions | 20% SR medium + 1% DMSO | 20% SR medium + 1% DMSO + 2.5 mM butyrate | 30 ng/mL HGF + 1% DMSO + 2.5 mM butyrate Strom's medium + 30 ng/mL hEGF + 10 ng/mL TGF-α + 30 ng/mL HGF + 1% DMSO + 2.5 mM butyrate |

Other additives tested in the subsequent (4-day) maturation step include factors such as FGF-4, and oncostatin M in the presence of dexamethazone.

FIG. 5 shows the hepatocyte-like cells that were obtained according to Protocol 7 detailed above, except that DMSO was not used in Stage IV. Left column: 10×magnification; Right column: 40×magnification. By 4 days in the presence of butyrate, more than 80% of cells in the culture are large in diameter, containing large nuclei and granular cytoplasm (Row A). After 5 days in SR medium, the cells were switched to HCM. Two days later, many cells are multi-nucleated, and have a large polygonal shape (Row B). By 4 days in HCM, multinucleated polygonal cells are common, and have a darker cytosol (Row C), by which criteria they resemble freshly isolated human adult hepatocytes (Row D) or fetal hepatocytes (Row E).

Example 10

Metabolic Enzyme Activity hES-derived hepatocyte lineage cells generated by the direct differentiation protocol were tested for cytochrome P450 activity.

After completion of the differentiation protocol, cells were cultured for 24-48 hours with or without 5 μM methylchloranthrene, an inducer for the cytochrome P-450 enzymes 1A1 and 1A2 (CYP1A1/2). Enzyme activity was measured as the rate of de-ethylation of ethoxyresorufin (EROD). The substrate was added to the medium at a concentration of 5 μM, and fluorescence of the culture supernatant was measured after 2 hours in a fluorimetric microplate reader at 355 nm excitation and 581 nm emission. The amount of resorufin formed was determined using a standard curve measured for purified resorufin, and expressed as picomoles resorufin formed per min per mg protein.

FIG. 6 shows the results. CYP1A1/2 activity was detected in the three hepatocyte lineage cell lines tested—two derived from the H1 ES cell line, and one derived from the H9 ES cell line. The level of activity was inducible by methylchloranthrene (MC), and exceeded the level observed in two preparations of freshly isolated human adult hepatocytes (HH). The level of activity in undifferentiated H1 and H9 cells (and in the BJ human embryonic fibroblast cell line) was negligible.

The hES-derived hepatocytes were transplanted under the kidney capsules of SCID mice ($2 \times 10^6$ cells under each capsule). Kidneys were harvested 10 days or 57 days later, and analyzed by immunohistology. Cytokeratin 8 and 19 staining was highly positive, while $\alpha_1$-antitrypsin staining was moderate and albumin staining was not detectable. Expression of cytokeratin 18 was not detected on day 10, but was evident by day 57. 89% of the cells were BrdU positive on day 10, but had declined to 18% on day 57.

Example 11

Kinetics of Differentiation

The length of time required for differentiated was assessed in the following experiment. hES cells were grown to confluence, pre-differentiated with 1% DMSO in 20% SR medium for 4 days, differentiated in 20% SR medium containing 1% DMSO and 2.5 mM butyrate for various periods, and then matured for 4 days in HCM containing 30 ng/mL hEGF, 10 ng/mL TGF-α, 30 ng/mL HGF, and 2.5 mM butyrate.

The phenotypic markers determined in the cells obtained are shown in Table 13.

TABLE 13

Markers on Cells under Different Differentiation Conditions

| % positive cells (immunocytochemistry) | 20% SR medium + 1% DMSO + 2.5 mM butyrate | |
|---|---|---|
| | 3 day differentiation | 6 day differentiation |
| Albumin | 52 ± 4% | 79 ± 6% |
| $\alpha_1$-antitrypsin | 76 ± 1% | 91 ± 2% |
| AFP | 34 ± 4% | 0% |
| CK8 | 91 ± 5% | 99 ± 1% |
| CK18 | 97 ± 1% | 94 ± 4% |
| CK19 | 99 ± 1% | 99 ± 1% |
| Desmin | 0% | 0% |
| Glycogen | 63 ± 5% | 70 ± 5% |
| Albumin level (ELISA) | 1.4 μg per $10^6$ cells | 0.6 μg per $10^6$ cells |

Levels of p450 enzymes were determined under contract by Tissue Transformation Technologies, Edison N.J. Results are shown in Table 14.

TABLE 14

Enzyme activity in Differentiated hES cells

|  | Primary hepatocytes #1 | Primary hepatocytes #2 | *Undifferentiated hES cells | hES derived Hepatocytes: Short Protocol | hES derived Hepatocytes: Long Protocol |
|---|---|---|---|---|---|
| CYP 1A2 | — | — | — | .020 | — |
| CYP 2A6 | 1.724 | 1.584 | — | .270 | .057 |
| CYP 2C19 | 1.107 | 0.268 | .105 | .527 | — |
| CYP 2D6 | 0.764 | 0.786 | .252 | .134 | .354 |
| ECOD | 1.647 | 2.477 | .267 | .142 | .027 |
| UGT | 13.185 | 27.329 | — | 3.964 | — |
| ST | 1.755 | 1.665 | — | .920 | — |
| GST | 16.562 | 18.134 | 9.174 | 46.964 | 21.208 |
| Uninduced EROD activity | 0 | 0 | 0 | 0.5 ± 0.1 | 0.3 ± 0.1 |
| Induced EROD activity | 3.2 ± 1.2 | 0.4 ± 0.0 | 0.7 ± 0.0 | 1.6 ± 0.5 | 0.8 ± 0.1 |

CYP 1A2 = 7-ethoxyresorufin O-deethylation
CYP 2A6 = coumarin 7-hydrozylation
CYP 2C19 = S-mephenytoin 4'-hydroxylation
CYP 2D6 = dextromethorphan O-demethylation
ECOD = 7-ethoxycoumarin O-deethylation
UGT = 7-hydroxycoumarin glucuronidation
ST = 7-hydroxycoumarin sulfation
GST = conjugation of reduced glutathione with 1-chloro-2,4,dinitrobenzene
EROD = de-ethylation of ethoxyresorufin (Units: nM EROD catalyzed per hour per $10^6$ cells)
"—" indicates no determination was made.

These data suggest that using a differentiation period of 3 days (the short protocol) rather than 6 days (the long protocol) produces hepatocyte-like cells with improved characteristics.

It will be recognized that the compositions and procedures described in this disclosure can effectively be modified by those skilled in the art without departing from the spirit of the invention embodied in the claims that follow.

What is claimed as the invention is:

1. A method for producing hepatocyte lineage cells from primate pluripotent stem (pPS) cells, comprising culturing the pPS cells in a medium comprising a hepatocyte lineage differentiation agent selected from sodium butyrate, n-butyric acid, trichosratin A, propionic acid, isobutyric acid, and isovaleric acid, wherein the method produces hepatocyte lineage cells; wherein the hepatocyte lineage cells have at least three of the following characteristics:
    antibody-detectable expression of $\alpha_1$-antitrypsin;
    antibody-detectable expression of albumin;
    absence of antibody-detectable expression of α-fetoprotein;
    RT-PCR detectable expression of asialoglycoprotein receptor;
    evidence of glycogen storage;
    evidence of cytochrome p450 activity;
    evidence of glucose-6-phosphatase activity; or the morphological features of hepatocytes.

2. The method of claim 1, wherein the hepatocyte lineage differentiation agent is sodium butyrate.

3. The method of claim 1, wherein differentiation is initiated in the pPS cells before the cells are cultured with the hepatocyte lineage differentiation agent.

4. The method of claim 3, wherein differentiation of the pPS cells is initiated by forming embryoid bodies.

5. The method of claim 3, wherein differentiation of the pPS cells is initiated by culturing in a medium containing dimethyl sulfoxide (DMSO), dimethylacetamide (DMA); hexamethylene bisacetamide, or another polymethylene bisacetamide.

6. The method of claim 1, comprising further culturing the hepatocyte lineage cells in a medium containing a cytokine or hormone selected from glucocorticoids, epidermal growth factor (EGF), insulin, TGF-α, TGF-β, fibroblast growth factor, hepatocyte growth factor (HGF), IL-1, IL-6, IGF-I, IGF-II, and HBGF-1.

7. The method of claim 6, wherein the hepatocyte lineage cells are cultured in a medium containing at least three of said cytokines or hormones.

8. The method of claim 7, wherein the hepatocyte lineage cells are cultured in a medium containing EGF, TGF-α, and HGF.

9. The method of claim 1, wherein the pPS cells are human embryonic stem cells.

10. The method of claim 1, further comprising maintaining the hepatocyte lineage cells by culturing them in a medium containing sodium butyrate.

* * * * *

UNITED STATES PATENT AND TRADEMARK OFFICE
CERTIFICATE OF CORRECTION

PATENT NO. : 7,256,042 B2 Page 1 of 1
APPLICATION NO. : 10/001267
DATED : August 14, 2007
INVENTOR(S) : Rambhatla et al.

It is certified that error appears in the above-identified patent and that said Letters Patent is hereby corrected as shown below:

Column 47, line 42, the word "trichosratin" should read --trichostatin--.

Signed and Sealed this

Twenty-seventh Day of November, 2007

JON W. DUDAS
*Director of the United States Patent and Trademark Office*